United States Patent
Park et al.

(10) Patent No.: US 12,042,332 B2
(45) Date of Patent: Jul. 23, 2024

(54) ULTRASOUND IMAGING APPARATUS, CONTROL METHOD THEREOF, AND COMPUTER PROGRAM

(71) Applicant: SAMSUNG MEDISON CO., LTD., Hongcheon-gun (KR)

(72) Inventors: Sungah Park, Seoul (KR); Eunho Yang, Seoul (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 44 days.

(21) Appl. No.: 17/132,653

(22) Filed: Dec. 23, 2020

(65) Prior Publication Data

US 2021/0282750 A1    Sep. 16, 2021

(30) Foreign Application Priority Data

Mar. 10, 2020    (KR) .......................... 10-2020-0029802

(51) Int. Cl.
*A61B 8/00* (2006.01)
*A61B 8/08* (2006.01)

(52) U.S. Cl.
CPC ............. *A61B 8/463* (2013.01); *A61B 8/465* (2013.01); *A61B 8/467* (2013.01); *A61B 8/5207* (2013.01)

(58) Field of Classification Search
CPC ......... A61B 8/463; A61B 8/465; A61B 8/467; A61B 8/5207; G16H 15/00; G16H 40/63
See application file for complete search history.

(56) References Cited

U.S. PATENT DOCUMENTS

| 5,813,986 | A | 9/1998 | Ubukata |
| 6,514,201 | B1 * | 2/2003 | Greenberg ............. G16H 40/63 600/437 |
| 7,455,403 | B2 | 11/2008 | Jones et al. |
| 7,455,406 | B2 | 11/2008 | Miwa et al. |

(Continued)

FOREIGN PATENT DOCUMENTS

| CN | 109636843 A | 4/2019 |
| EP | 3 150 128 A1 | 4/2017 |

(Continued)

OTHER PUBLICATIONS

Angtuaco TL et al: "Congenifal urinary tract abnormalities: Prenatal and neonatal diagnosis", Sep. 1990 (Year: 1990).*

(Continued)

*Primary Examiner* — Serkan Akar
*Assistant Examiner* — Gabriel Victor Popescu
(74) *Attorney, Agent, or Firm* — Sughrue Mion, PLLC

(57) ABSTRACT

Provided are an ultrasound imaging apparatus and a control method thereof, the ultrasound imaging apparatus including: an input/output interface; a storage; and at least one processor configured to: display, via the input/output interface, at least one resulting value calculated based on a plurality of medical images when one of the at least one resulting value is selected by an input via the input/output interface, retrieve, from the storage, a plurality of measurement values and a plurality of medical images used to calculate the selected resulting value; and output, via the input/output interface, the retrieved plurality of measurement values and the retrieved plurality of medical images on a single display.

9 Claims, 18 Drawing Sheets

(56) References Cited

U.S. PATENT DOCUMENTS

| | | | |
|---|---|---|---|
| 2005/0038342 A1* | 2/2005 | Mozayeni | A61B 8/0808 600/454 |
| 2006/0235301 A1* | 10/2006 | Chalana | A61B 8/0866 600/433 |
| 2007/0277127 A1 | 11/2007 | Carlson et al. | |
| 2009/0012393 A1 | 1/2009 | Choi | |
| 2013/0261447 A1* | 10/2013 | Tashiro | A61B 8/463 600/437 |
| 2014/0088428 A1* | 3/2014 | Yang | A61B 8/465 600/443 |
| 2014/0121524 A1* | 5/2014 | Chiang | A61B 8/467 600/459 |
| 2016/0345936 A1* | 12/2016 | Cho | A61B 8/463 |
| 2017/0372473 A1 | 12/2017 | Ujiie et al. | |
| 2018/0021022 A1 | 1/2018 | Lundberg et al. | |
| 2018/0161010 A1 | 6/2018 | Choi et al. | |
| 2019/0029648 A1 | 1/2019 | Kurosaki et al. | |
| 2019/0192117 A1* | 6/2019 | Tashiro | A61B 8/463 |
| 2019/0200960 A1* | 7/2019 | Kang | A61B 8/483 |
| 2019/0216436 A1* | 7/2019 | Miyazawa | A61B 8/463 |
| 2019/0247025 A1* | 8/2019 | Jin | A61B 8/463 |
| 2020/0219279 A1 | 7/2020 | Ebata | |

FOREIGN PATENT DOCUMENTS

| | | | |
|---|---|---|---|
| JP | 2007-316637 A | 12/2007 |
| JP | 5300171 B2 | 9/2013 |
| JP | 2018-943 A | 1/2018 |
| KR | 10-1055589 B1 | 8/2011 |
| KR | 10-1922180 B1 | 11/2018 |
| WO | 2019/078054 A1 | 4/2019 |

OTHER PUBLICATIONS

U-King-Im J M et al: "Carotid-artery imaging in the diagnosis and management of patients at risk of stroke", Sep. 1990 (Year: 1990).*
U-King-Im et al., "Carotid-artery imaging in the diagnosis and management of patients at risk of stroke," Lancet Neurology, vol. 8, No. 6, pp. 569-580, Jun. 2009, XP026107670.
Angtuaco et al., "Congenital Urinary Tract Abnormalities: Prenatal and Neonatal Diagnosis," Current Problems in Diagnostic Radiology, vol. 19, No. 5, pp. 170-198, Sep. 1990, XP023060843.
Communication dated Jun. 23, 2021, issued by the European Patent Office in counterpart European Application No. 20217067.6.
European Extended Search Report issued Nov. 9, 2023 issued by the European Patent Office for EP Patent Application No. 20217067.6.

* cited by examiner

ULTRASOUND IMAGING APPARATUS, CONTROL METHOD THEREOF, AND COMPUTER PROGRAM

CROSS-REFERENCE TO RELATED APPLICATION(S)

This application is based on and claims priority under 35 U.S.C. § 119 to Korean Patent Application No. 10-2020-0029802, filed on Mar. 10, 2020, in the Korean Intellectual Property Office, the disclosure of which is incorporated by reference herein in its entirety.

BACKGROUND

1. Field

Embodiments of the disclosure relate to ultrasound imaging apparatuses, control methods of an ultrasound imaging apparatus, and computer programs for performing the methods.

2. Description of Related Art

Ultrasound imaging apparatuses are designed to facilitate capturing of medical images in various views. Due to the convenience in image capturing, ultrasound imaging apparatuses have been widely used to capture medical images in various views while a user examines the medical images in real-time. Furthermore, an ultrasound imaging apparatus provides a function for automatically or manually obtaining a desired measurement value from an ultrasound image. The user may obtain various measurement values by selecting a measurement point from an ultrasound image acquired in a desired view. Furthermore, the ultrasound imaging apparatus uses a predefined function to calculate a resulting value from a plurality of measurement values obtained from a plurality of ultrasound images. However, when a plurality of ultrasound images and a plurality of measurement values are used to calculate a resulting value, the user is inconvenienced in having to go through multiple manipulation operations in order to individually check the ultrasound images and measurement values related to the resulting value.

SUMMARY

Provided are ultrasound imaging apparatuses, control methods thereof, and computer programs for conveniently providing a plurality of relevant ultrasound images and a plurality of measurement values for a resulting value calculated by an ultrasound imaging apparatus based on the relevant ultrasound images and measurement values.

Also provided are ultrasound imaging apparatuses, control methods thereof, and computer programs, which are capable of conveniently viewing, when a plurality of ultrasound images are captured and a plurality of measurement values are obtained to calculate a resulting value, the ultrasound images and the measurement values after completing a scan.

Additional aspects will be set forth in part in the description which follows and, in part, will be apparent from the description, or may be learned by practice of the presented embodiments of the disclosure.

In accordance with an aspect of the disclosure, an ultrasound imaging apparatus includes: an input/output interface; a storage; and at least one processor configured to: display, via the input/output interface, at least one resulting value calculated based on a plurality of medical images when one of the at least one resulting value is selected by an input via the input/output interface, retrieve, from the storage, a plurality of measurement values and a plurality of medical images used to calculate the selected resulting value; and output, via the input/output interface, the retrieved plurality of measurement values and the retrieved plurality of medical images on a single display.

The plurality of medical images may be stored in the storage together with at least one of attribute information, measurement value information, and scanning protocol information related to the plurality of medical images, or a combination thereof, and the at least one processor may be further configured to retrieve the plurality of medical images used to calculate the selected resulting value from the storage, based on the at least one of the attribute information, the measurement value information, and the scanning protocol information related to the plurality of medical images, or the combination thereof.

The ultrasound imaging apparatus may further include a probe configured to output ultrasound signals to an object and detect echo signals reflected from the object, and the at least one processor may be further configured to generate at least one ultrasound image based on the echo signals and store the at least one ultrasound image and at least one measurement value related to the at least one ultrasound image in the storage.

The plurality of medical images may include the at least one ultrasound image, and the at least one processor may be further configured to: calculate the at least one resulting value based on the at least one ultrasound image and the at least one measurement value related to the at least one ultrasound image; and display a real-time scan image and the at least one resulting value via the input/output interface.

The at least one processor may be further configured to: display, based on a user input for selecting one of the displayed at least one resulting value, at least one ultrasound image and at least one measurement value related to the selected resulting value; and provide, via the input/output interface, at least one of a rescanning menu for the at least one ultrasound image related to the selected resulting value and a remeasurement menu for the at least one measurement value related to the selected resulting value, or a combination of the rescanning menu and the remeasurement menu.

The at least one processor may be further configured to: store an ultrasound image recaptured based on the rescanning menu in the storage; and update the at least one measurement value and the at least one resulting value based on the recaptured ultrasound image.

The at least one processor may be further configured to output, via the input/output interface, a required ultrasound image list and a required measurement value list corresponding to a scanning protocol selected via the input/output interface.

The at least one processor may be further configured to: output, based on a selection of an ultrasound image item from the required ultrasound image list, an ultrasound image corresponding to the selected ultrasound image item via the input/output interface; and output, based on a selection of a measurement value item from the required measurement value list, an ultrasound image corresponding to the selected measurement value item via the input/output interface.

The at least one processor may be further configured to: produce a first resulting value by using a plurality of medical images generated based on the echo signals; and output, via the input/output interface, the plurality of medical images required to produce the first resulting value and the first resulting value on a single display based on a trigger condition that the generating of the plurality of medical images and the producing of the first resulting value are completed The at least one resulting value may include an internal carotid artery (ICA)/common carotid artery (CCA) peak systolic velocity (PSV) ratio that is a ratio between an ICA PSV and a CCA PSV, and the at least one processor may be further configured to: output the ICA/CCA PSV ratio via the input/output interface; and output, based on an input signal for selecting the ICA/CCA PSV ratio, a first ultrasound image in which the ICA PSV is measured, a time-blood flow velocity spectrum of ICA, a second ultrasound image in which the CCA PSV is measured, and a time-blood flow velocity spectrum of CCA on the single display.

The at least one resulting value may include the ICA/CCA PSV ratio that is a ratio between the ICA PSV and the CCA PSV, and the at least one processor may be further configured to: output the ICA/CCA PSV ratio via the input/output interface; and output, based on an input signal for selecting the ICA/CCA PSV ratio, a time-blood flow velocity spectrum of ICA and a time-blood flow velocity spectrum of CCA on the single display.

The at least one resulting value may include an amniotic fluid index (AFI) in a pregnant woman, and the at least one processor may be further configured to: output the AFI via the input/output interface; and output, based on an input signal for selecting the AFI, a plurality of ultrasound images used to measure the AFI on the single display.

In accordance with another aspect of the disclosure, a control method of an ultrasound imaging apparatus includes: displaying at least one resulting value calculated based on a plurality of medical images; when one of the at least one resulting value is selected by an input via an input/output interface, retrieving, from a storage, a plurality of measurement values and a plurality of medical images used to calculate the selected resulting value; and outputting, via the input/output interface, the retrieved plurality of measurement values and the retrieved plurality of medical images on a single display.

In accordance with another aspect of the disclosure, a computer program stored in a recording medium includes at least one instruction which, when executed by a processor, causes the processor to perform a control method of an ultrasound imaging apparatus.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
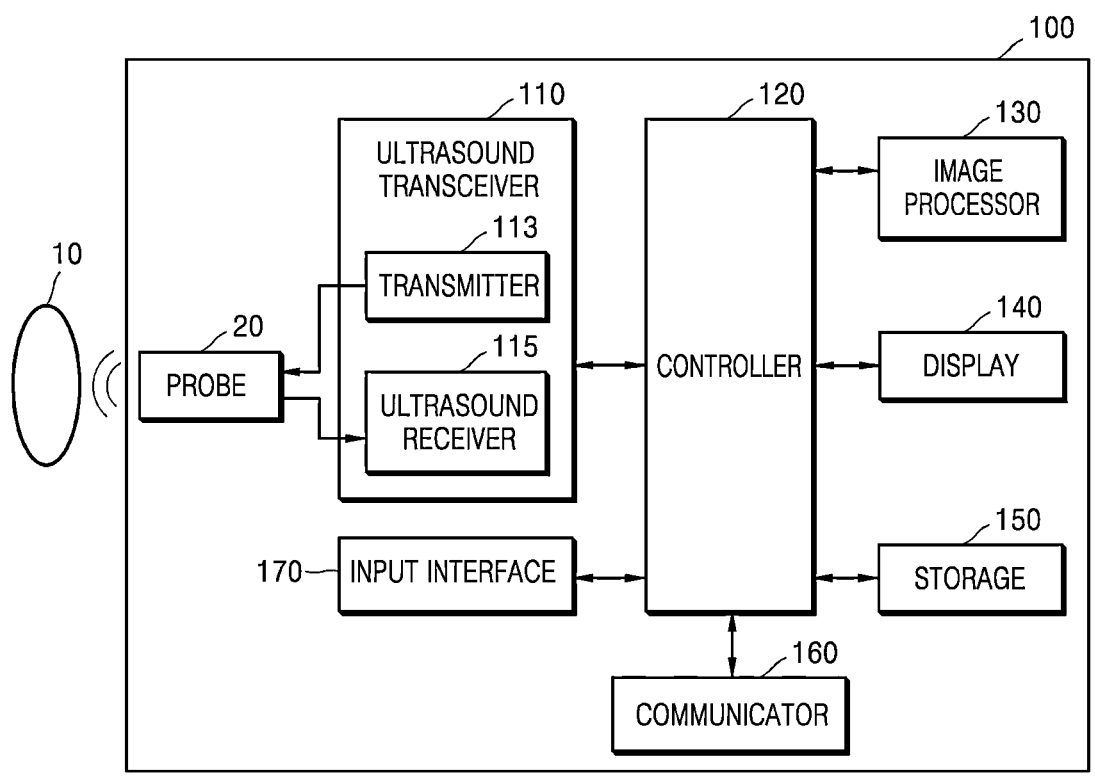
FIG. 1 is a block diagram of a configuration of an ultrasound imaging apparatus according to an embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

Terms such as "part" and "portion" used herein denote those that may be embodied by software or hardware. According to exemplary embodiments, a plurality of parts or portions may be embodied by a single unit or element, or a single part or portion may include a plurality of elements.

Expressions such as "at least one of," when preceding a list of elements, modify the entire list of elements and do not modify the individual elements of the list.

In exemplary embodiments, an image may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object", which is a thing to be imaged, may include a human, an animal, or a part thereof. For example, an object may include a part of a human, that is, an organ or a tissue, or a phantom.

Throughout the specification, an ultrasound image refers to an image of an object processed based on ultrasound signals transmitted to the object and reflected therefrom.

FIG. 1 is a block diagram illustrating a configuration of an ultrasound diagnosis apparatus 100, i.e., a diagnostic apparatus, according to an exemplary embodiment.

Referring to FIG. 1, the ultrasound diagnosis apparatus 100 may include a probe 20, an ultrasound transceiver 110, a controller 120, an image processor 130, one or more displays 140, a storage 150, e.g., a memory, a communicator 160, i.e., a communication device or an interface, and an input interface 170.

The ultrasound diagnosis apparatus 100 may be of a cart-type or a portable-type ultrasound diagnosis apparatus, that is portable, moveable, mobile, or hand-held. Examples of the portable-type ultrasound diagnosis apparatus 100 may include a smart phone, a laptop computer, a personal digital assistant (PDA), and a tablet personal computer (PC), each of which may include a probe and a software application, but embodiments are not limited thereto.

The probe 20 may include a plurality of transducers. The plurality of transducers may transmit ultrasound signals to an object 10 in response to transmitting signals received by the probe 20, from a transmitter 113. The plurality of transducers may receive ultrasound signals reflected from the object 10 to generate reception signals. In addition, the probe 20 and the ultrasound diagnosis apparatus 100 may be formed in one body (e.g., disposed in a single housing), or the probe 20 and the ultrasound diagnosis apparatus 100 may be formed separately (e.g., disposed separately in separate housings) but linked wirelessly or via wires. In addition, the ultrasound diagnosis apparatus 100 may include one or more probes 20 according to embodiments.

The controller 120 may control the transmitter 113 for the transmitter 113 to generate transmitting signals to be applied to each of the plurality of transducers based on a position and a focal point of the plurality of transducers included in the probe 20.

The controller 120 may control the ultrasound receiver 115 to generate ultrasound data by converting reception signals received from the probe 20 from analogue to digital signals and summing the reception signals converted into digital form, based on a position and a focal point of the plurality of transducers.

The image processor 130 may generate an ultrasound image by using ultrasound data generated from the ultrasound receiver 115.

The display 140 may display a generated ultrasound image and various pieces of information processed by the ultrasound diagnosis apparatus 100. The ultrasound diagnosis apparatus 100 may include two or more displays 140 according to the present exemplary embodiment. The display 140 may include a touch screen in combination with a touch panel.

The controller 120 may control the operations of the ultrasound diagnosis apparatus 100 and flow of signals between the internal elements of the ultrasound diagnosis apparatus 100. The controller 120 may include a memory for storing a program or data to perform functions of the ultrasound diagnosis apparatus 100 and a processor and/or a microprocessor (not shown) for processing the program or data. For example, the controller 120 may control the operation of the ultrasound diagnosis apparatus 100 by receiving a control signal from the input interface 170 or an external apparatus.

The ultrasound diagnosis apparatus 100 may include the communicator 160 and may be connected to external apparatuses, for example, servers, medical apparatuses, and portable devices such as smart phones, tablet personal computers (PCs), wearable devices, etc., via the communicator 160.

The communicator 160 may include at least one element capable of communicating with the external apparatuses. For example, the communicator 160 may include at least one among a short-range communication module, a wired communication module, and a wireless communication module.

The communicator 160 may receive a control signal and data from an external apparatus and transmit the received control signal to the controller 120 so that the controller 120 may control the ultrasound diagnosis apparatus 100 in response to the received control signal.

The controller 120 may transmit a control signal to the external apparatus via the communicator 160 so that the external apparatus may be controlled in response to the control signal of the controller 120.

For example, the external apparatus connected to the ultrasound diagnosis apparatus 100 may process the data of the external apparatus in response to the control signal of the controller 120 received via the communicator 160.

A program for controlling the ultrasound diagnosis apparatus 100 may be installed in the external apparatus. The program may include command languages to perform part of operation of the controller 120 or the entire operation of the controller 120.

The program may be pre-installed in the external apparatus or may be installed by a user of the external apparatus by downloading the program from a server that provides applications. The server that provides applications may include a recording medium where the program is stored.

The storage 150 may store various data or programs for driving and controlling the ultrasound diagnosis apparatus 100, input and/or output ultrasound data, ultrasound images, applications, etc.

The input interface 170 may receive a user's input to control the ultrasound diagnosis apparatus 100 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but an exemplary embodiment is not limited thereto.

An example of the ultrasound diagnosis apparatus 100 according to the present exemplary embodiment is described below with reference to FIGS. 2A, 2B, and 2C.

Figure 2A:
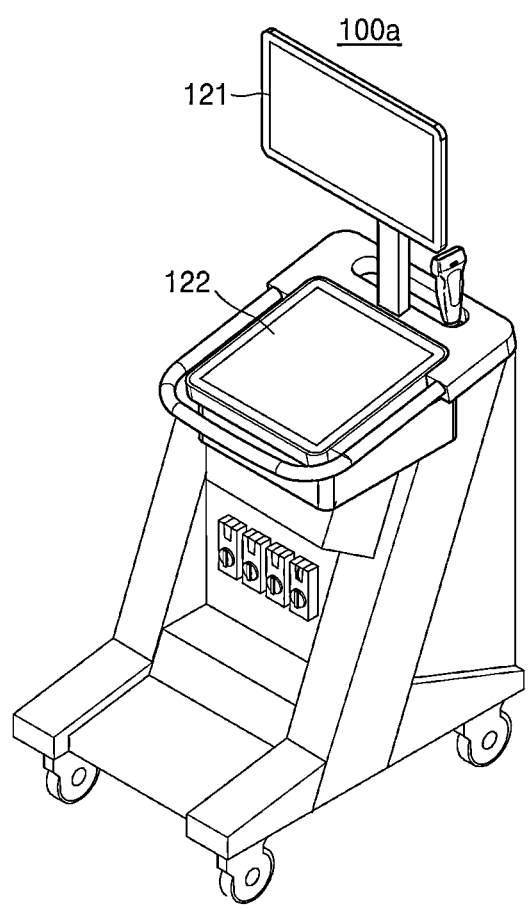
FIGS. 2A through 2C illustrate ultrasound imaging apparatuses according to embodiments.
Figure 2B:
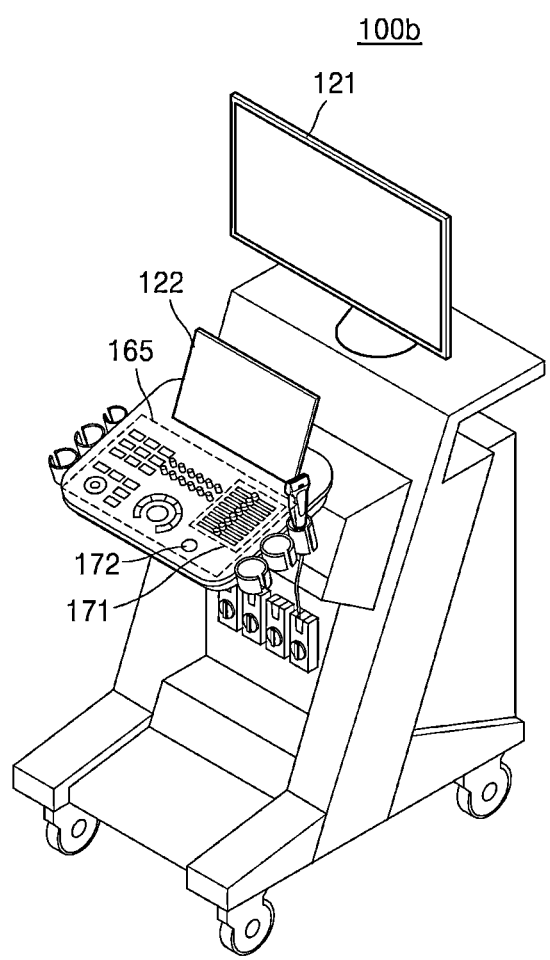
Figure 2C:
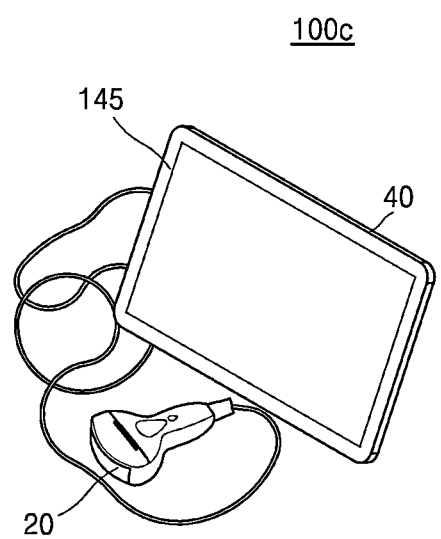

FIGS. 2A, 2B, and 2C are diagrams illustrating ultrasound diagnosis apparatus according to an exemplary embodiment.

Referring to FIGS. 2A and 2B, the ultrasound diagnosis apparatus 100a and 100b may include a main display 121 and a sub-display 122. At least one among the main display 121 and the sub-display 122 may include a touch screen. The main display 121 and the sub-display 122 may display ultrasound images and/or various information processed by the ultrasound diagnosis apparatus 100a and 100b. The main display 121 and the sub-display 122 may provide graphical user interfaces (GUI), thereby receiving user's inputs of data to control the ultrasound diagnosis apparatus 100a and 100b. For example, the main display 121 may display an ultrasound image and the sub-display 122 may display a control panel to control display of the ultrasound image as a GUI. The sub-display 122 may receive an input of data to control the display of an image through the control panel displayed as a GUI. The ultrasound diagnosis apparatus 100a and 100b may control the display of the ultrasound image on the main display 121 by using the input control data.

Referring to FIG. 2B, the ultrasound diagnosis apparatus 100b may include a control panel 165. The control panel 165 may include buttons, trackballs, jog switches, or knobs, and may receive data to control the ultrasound diagnosis apparatus 100b from the user. For example, the control panel 165 may include a time gain compensation (TGC) button 171 and a freeze button 172. The TGC button 171 is to set a TGC value for each depth of an ultrasound image. Also, when an input of the freeze button 172 is detected during scanning an ultrasound image, the ultrasound diagnosis apparatus 100b may keep displaying a frame image at that time point.

The buttons, trackballs, jog switches, and knobs included in the control panel 165 may be provided as a GUI to the main display 121 or the sub-display 122.

Referring to FIG. 2C, the ultrasound diagnosis apparatus 100c may include a portable device. An example of the portable ultrasound diagnosis apparatus 100c may include, for example, smart phones including probes and applications, laptop computers, personal digital assistants (PDAs), or tablet PCs, but an exemplary embodiment is not limited thereto.

The ultrasound diagnosis apparatus 100c may include the probe 20 and a main body 40. The probe 20 may be connected to one side of the main body 40 by wire or wirelessly. The main body 40 may include a touch screen 145. The touch screen 145 may display an ultrasound image, various pieces of information processed by the ultrasound diagnosis apparatus 100c, and a GUI.

Figure 3:
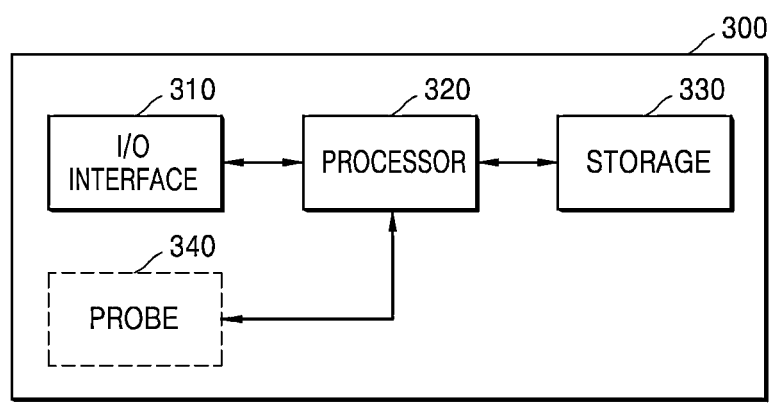
FIG. 3 is a block diagram of a structure of an ultrasound imaging apparatus according to an embodiment of the disclosure.

FIG. 3 is a block diagram of a structure of an ultrasound imaging apparatus 300 according to an embodiment of the disclosure.

According to an embodiment of the disclosure, the ultrasound imaging apparatus 300 includes an input/output (I/O) interface 310, a processor 320, and a storage 330. According to an embodiment, the ultrasound imaging apparatus 300 may further include a probe 340, but in another embodiment, it may not include the probe 340. In the disclosure, although the ultrasound imaging apparatus 300 is mainly described with respect to an embodiment in which the ultrasound imaging apparatus 300 includes the probe 340, but embodiments of the disclosure are not limited thereto.

The I/O interface 310 receives an input from an external device or user, and outputs data and signals. The I/O interface 310 includes at least one of at least one input device and at least one output device, or a combination thereof. For example, the I/O interface 310 may correspond to the input interface 170 and the display 140 described with reference to FIG. 1. Furthermore, the I/O interface 310 may correspond to the main display 121 and the sub-display 122 of FIGS. 2A and 2B, and may be implemented as a touch screen. In addition, the I/O interface 310 may correspond to the control panel 165 of FIG. 2B or the touch screen 145 of FIG. 2C.

The I/O interface 310 transmits a received input signal to the processor 320 and outputs data output from the processor 320. The I/O interface 310 displays at least one resulting value and receives an input for selecting one of the displayed resulting values. Furthermore, the I/O interface 310 displays a plurality of medical images and a plurality of measurement values related to the selected resulting value. The medical images and the measurement values related to the selected resulting value may be output on a single display in one GUI view.

In the disclosure, a measurement value refers to a value automatically or manually measured in a medical image. The user may obtain a certain measurement value by defining a reference point or reference line for the measurement value in the medical image. The processor 320 may define a measurement value based on a reference point or reference line input by a user. For example, when a measurement value is a certain length and the user inputs a start point and an end point of the certain length, the processor 320 may define a length between the start point and the end point input by the user as the certain length. As another example, the processor 320 may automatically obtain a measurement value by detecting a predefined anatomical structure in a medical image. In detail, the processor 320 may automatically perform segmentation on a medical image or automatically detect a predefined anatomical point in the medical image to thereby automatically obtain a measurement value based on the segmentation result or detected anatomical point.

According to the disclosure, the resulting value is a value calculated using at least one measurement value obtained from a medical image. Measurement values and equations required to calculate a resulting value are predefined.

The processor 320 controls all operations of the ultrasound imaging apparatus 300. The processor 320 may be implemented as one or more processors. The processor 320 receives ultrasound signals from the probe 340 to reconstruct an ultrasound image. The ultrasound signals generated by the probe 340 undergo predefined signal processing via a beamformer, an amplifier, an analog-to-digital converter, etc., and are then transmitted to the processor 320. The processor 320 may perform a preset operation by executing an instruction or command stored in a memory. According to an embodiment, the processor 320 may correspond to the controller 120 and the image processor 130 of FIG. 1.

The processor 320 generates at least one medical image based on echo signals. The medical image corresponds to an ultrasound image.

The processor 320 displays, via the I/O interface 310, at least one resulting value calculated based on a plurality of medical images. The processor 320 may display at least one resulting value based on a preset operation mode or a user's control input. For example, the user may select an operation mode or menu for retrieving a resulting value, and the processor 320 displays at least one resulting value according to the selected operation mode or menu.

Furthermore, when an input for selecting a resulting value is received via the I/O interface 310, the processor 320 retrieves a plurality of medical images used to calculate the selected resulting value from the storage 330. The input for selecting the resulting value may be performed in various forms, such as an input via a mouse, a touch input, an input via a key button, an input via a dial, etc. When the resulting value is selected, the processor 320 determines and retrieves at least one measurement value required to calculate the resulting value. The measurement value required to calculate the resulting value may be determined from a list of values required for an equation for calculating the resulting value. Furthermore, the processor 320 retrieves at least one measurement value for a patient corresponding to the resulting value, based on patient identification information corresponding to the resulting value. The processor 320 also retrieves at least one relevant medical image used to obtain the at least one measurement value for the patient corresponding to the resulting value. The relevant medical image may be retrieved based on the patient identification information and a type of the measurement value. A file in which each resulting value is stored may also include storage path information or identification information regarding at least one measurement value and at least one relevant medical image used to calculate the resulting value. In addition, each resulting value and at least one measurement value and at least one medical image corresponding to the resulting value may be stored and defined together with their acquisition dates and patient identification information.

A plurality of medical images may be stored together with at least one of attribute information, measurement value information, and scanning protocol information related to the medical images, or a combination thereof. The attribute information of the medical images may include information such as date and time when the medical images were captured, patient identification information, a file name, and resolution of the medical images. The measurement value information may include a type of measurement values respectively obtained from the medical images, numerical measurement values, measurement points, etc. The scanning protocol information may include information about a type of scanning protocol used to capture the medical images. When retrieving a plurality of medical images, the processor 320 may use at least one of attribute information, measurement value information, and scanning protocol information, which are stored together with the medical images, or a combination thereof. When the user selects a resulting value, information about a plurality of measurement values used to calculate the resulting value may be determined, and a plurality of relevant medical images for obtaining the measurement values may be defined by at least one of attribute information, measurement value information, and a scanning protocol related to the medical images, or a combination thereof. The processor 320 retrieves the relevant medical images from the storage 330 based on information used to define the relevant medical images. For example, the processor 320 may retrieve the relevant medical images from the storage 330 based on a combination of a type of the measurement values, date and time of imaging, and a patient identification number.

Furthermore, the processor 320 outputs the retrieved measurement values and medical images on a single display via the I/O interface 310. The retrieved medical images are respectively displayed in different regions of a GUI view. For example, the processor 320 may define first through fourth regions that do not overlap one another in the GUI view and respectively display first through fourth medical images in the first through fourth regions. Furthermore, the processor 320 displays, together in each region of the GUI view, a measurement value obtained from a medical image displayed in the region. For example, a first measurement value obtained from the first image may be displayed in the first region, and a second measurement value obtained from the second image may be displayed in the second region. The processor 320 displays information about the selected resulting value together in the GUI view where the medical images and the measurement values are displayed.

Furthermore, the processor 320 controls a scan mode of the ultrasound imaging apparatus 300. The processor 320 may generate a medical image based on echo signals received via the probe 340. Furthermore, the processor 320 may provide a GUI for obtaining a measurement value from a medical image and define and generate the measurement value based on an input. Furthermore, the processor 320 may calculate a resulting value from at least one measurement value. The processor 320 stores generated medical images, measurement values, and resulting values in the storage 330.

The storage 330 stores data, computer program instructions, commands, control signals, or the like. The storage 330 may include a volatile storage medium, a non-volatile storage medium, or a combination thereof. The storage 330 may be implemented as various types of storage media. The storage 330 may include at least one of a flash memory-type memory, a hard disk-type memory, a multimedia card micro-type memory, a card-type memory (e.g., an SD card or an XD memory), random access memory (RAM), static RAM (SRAM), read-only memory (ROM), electrically erasable programmable ROM (EEPROM), PROM, a magnetic memory, a magnetic disc, and an optical disc, or a combination thereof.

The storage 330 stores a plurality of medical images, a plurality of measurement values, and a plurality of resulting values. A plurality of medical images may be stored together with at least one of attribute information, measurement value information, and scanning protocol information related to the relevant medical images, or a combination thereof. Furthermore, the storage 330 may store information about a scanning protocol and a list of required ultrasound images and a list of required measurement values corresponding to the scanning protocol.

The probe 340 including an array of a plurality of transducers transmits ultrasound signals to an object and detects echo signals reflected from the object. The probe 340 may correspond to the probe 20 of FIG. 1. According to embodiments of the disclosure, the probe 340 may correspond to a two-dimensional (2D) probe having an array of one row of transducers, or a three-dimensional (3D) probe having a 2D array of m×n transducers (where m and n are natural numbers).

Figure 4:
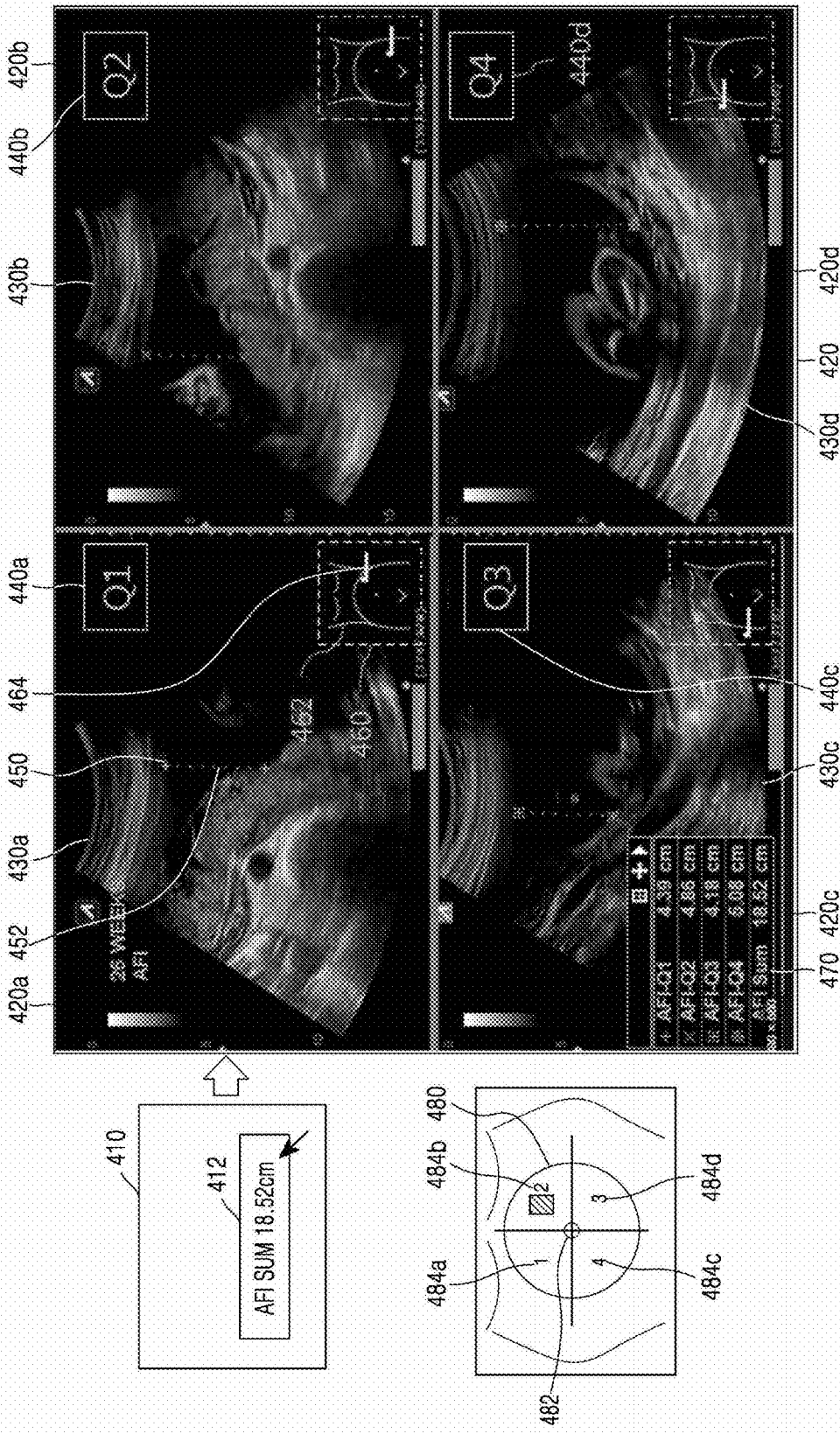
FIG. 4 illustrates a graphical user interface (GUI) view for displaying a plurality of medical images and a plurality of measurement values, according to an embodiment of the disclosure.

FIG. 4 illustrates a GUI view for displaying a plurality of medical images and a plurality of measurement values, according to an embodiment of the disclosure.

According to an embodiment, when a user selects a previously calculated resulting value 412 displayed in a first GUI view 410, the ultrasound imaging apparatus 300 displays a second GUI view 420 for displaying a plurality of relevant medical images, i.e., first through fourth medical images 430a through 430d, and measurement values 470 used to calculate the resulting value 412. The second GUI view 420 includes a plurality of regions, i.e., first through fourth regions 420a through 420d, which do not overlap one other, and the first through fourth medical images 430a through 430d are respectively displayed in the first through fourth regions 420a through 420d.

The ultrasound imaging apparatus 300 may provide information about the resulting value 412 during ultrasound imaging. As another example, the ultrasound imaging apparatus 300 may provide information about the resulting value 412 in a report mode. The resulting value 412 may be displayed together with medical images or other information or images.

FIG. 4 illustrates an example in which the resulting value 412 is an amniotic fluid index (AFI). AFI is used to diagnose oligohydramnios or polyhydramnios. Because the AFI is calculated by dividing an abdomen 480 into a plurality of regions and summing amniotic fluid volumes measured in the regions, a total amniotic fluid volume is expressed as AFI SUM. In order to calculate the AFI SUM, the ultrasound imaging apparatus 300 defines first through fourth abdominal quadrants 484a through 484d by dividing an abdomen 480 into four regions with a navel 482 as a central point, measures a largest diameter of an amniotic fluid pocket (excluding umbilical cord and fetal body parts) in each of the first through fourth abdominal quadrants 484a through 484d, and adds together lengths of largest amniotic fluid pockets respectively measured in first through fourth abdominal quadrants 484a through 484d. To obtain an AFI SUM value, the user measures a length of a largest amniotic fluid pocket in each of the four quadrants 484a through 484d by using a medical image obtained by the ultrasound imaging apparatus 300. The user inputs measurement points 450 for measuring a length of a largest amniotic fluid pocket to the ultrasound imaging apparatus 300. The ultrasound imaging apparatus 300 defines a distance 452 between two end points from among the measurement points 450 input by the user as a length of a largest amniotic fluid pocket. Lengths of largest amniotic fluid pockets measured in the first through fourth medical images 430a through 430d respectively corresponding to the first through fourth abdominal quadrants 484a through 484d are defined as the measurement values 470. For example, an AFI value measured in the first abdominal quadrant 484a is defined as AFI_Q1, an AFI value measured in the second abdominal quadrant 484b is defined as AFI_Q2, an AFI value measured in the third abdominal quadrant 484c is defined as AFI_Q3, and an AFI value measured in the fourth abdominal quadrant 484d is defined as AFI_Q4. When the AFI_Q1 through AFI_Q4 values are all obtained, the ultrasound imaging apparatus 300 calculates the AFI SUM from the obtained the AFI_Q1 through AFI_Q4 values.

According to an embodiment of the disclosure, the AFI SUM that is the resulting value 412 is displayed in the first GUI view 410, and when the user selects the AFI SUM, the ultrasound imaging apparatus 300 respectively displays, in the first through fourth regions 420a through 420d of the second GUI view 420, the first through fourth medical images 430a through 430d respectively used when measuring the AFI_Q1 through AFI_Q4 values in the first through fourth abdominal quadrants 484a through 484d.

Furthermore, the ultrasound imaging apparatus 300 displays the AFI_Q1 through AFI_Q4 values as the measurement values 470 in the second GUI view 420. As shown in FIG. 4, the AFI_Q1 through AFI_Q4 values may be displayed together in a region of the second GUI view 420. As another example, the AFI_Q1 through AFI_Q4 values may be respectively displayed as the measurement values 470 in regions where medical images corresponding to the measurement values 470 are displayed. For example, the AFI_Q1 through AFI_Q4 values may be respectively displayed in the first through fourth regions 420a through 420d.

According to an embodiment, the ultrasound imaging apparatus 300 displays indicators 440a through 440d indicating abdominal quadrants respectively corresponding to the first through fourth regions 420a through 420d.

According to an embodiment, the ultrasound imaging apparatus 300 displays scan location information 460 indicating a location where each of the first through fourth medical images 430a through 430d corresponding to one of the first through fourth regions 420a through 420d is captured. The scan location information 460 may include an object shape 462 and a probe indicator 464 corresponding to the probe 340. The probe indicator 464 may provide information about a scan location because its position changes according to the scan location.

Figure 5:
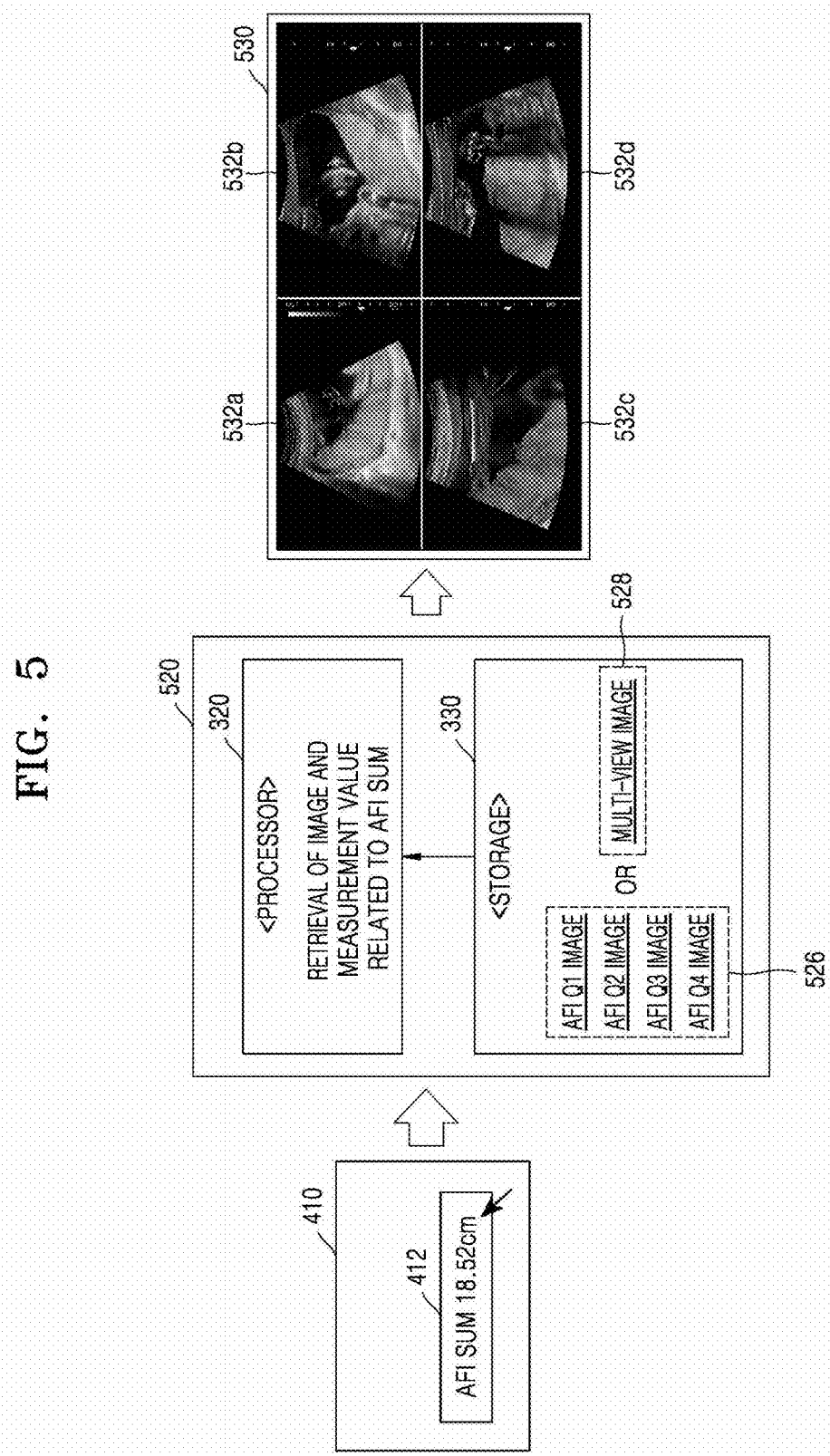
FIG. 5 illustrates a process of retrieving at least one relevant medical image and at least one measurement value corresponding to a selected resulting value, according to an embodiment of the disclosure.

FIG. 5 illustrates a process of retrieving at least one relevant medical image and at least one measurement value corresponding to a selected resulting value, according to an embodiment of the disclosure.

According to an embodiment, when a resulting value 412 is selected by the user, the ultrasound imaging apparatus 300 may retrieve, from the storage 330, at least one measurement value and at least one relevant medical image used to calculate the selected resulting value 412. Information about the at least one measurement value and the at least one relevant medical image used as a basis for calculating the resulting value 412 may be stored as meta information together with the resulting value 412. For example, information about the at least one relevant measurement value and the at least one relevant medical image may be stored in various forms, such as a header or meta information for a file in which the resulting value 412 is stored.

According to an embodiment, the at least one relevant measurement value itself may be stored together as meta information for the resulting value 412. For example, AFI_Q1 through AFI_Q4 values may be stored together with an AFI SUM value.

According to another embodiment, the at least one relevant measurement value may be stored together with the at least one relevant medical image from which the measurement value is obtained, and the processor 320 may retrieve the relevant measurement value stored in the relevant medical image and then use the relevant measurement value.

According to an embodiment, the at least one relevant medical image, i.e., AFI Q1 through AFI Q4 images, may be respectively stored as individual files 526. The processor 320 retrieves the individual files 526 of the at least one relevant medical image, i.e., AFI Q1 through AFI Q4 images, from the storage 330 by using information about the relevant medical image, which is stored in the resulting value 412 selected by the user. In this case, the processor 320 may respectively place the at least one relevant medical image, i.e., AFI Q1 through AFI Q4 images, stored in the individual files 526 in a plurality of regions 532a through 532d of a second GUI view 530.

According to another embodiment, a multi-view image in which relevant medical images are placed in the regions 532a through 532d may be stored as a single file 528. In this case, for each resulting value, a multi-view image may be generated by synthesizing relevant medical images placed in a plurality of regions and then stored in the storage 330. After calculating a resulting value, the processor 320 may generate a multi-view image by placing, in a plurality of regions, at least one medical image used as a basis for calculating the resulting value, and then store the multi-view image together with the resulting value in the storage 330. Each resulting value may include information (a storage path, a file name, etc.) about the file 528 of the multi-view image corresponding to the resulting value.

Figure 6:
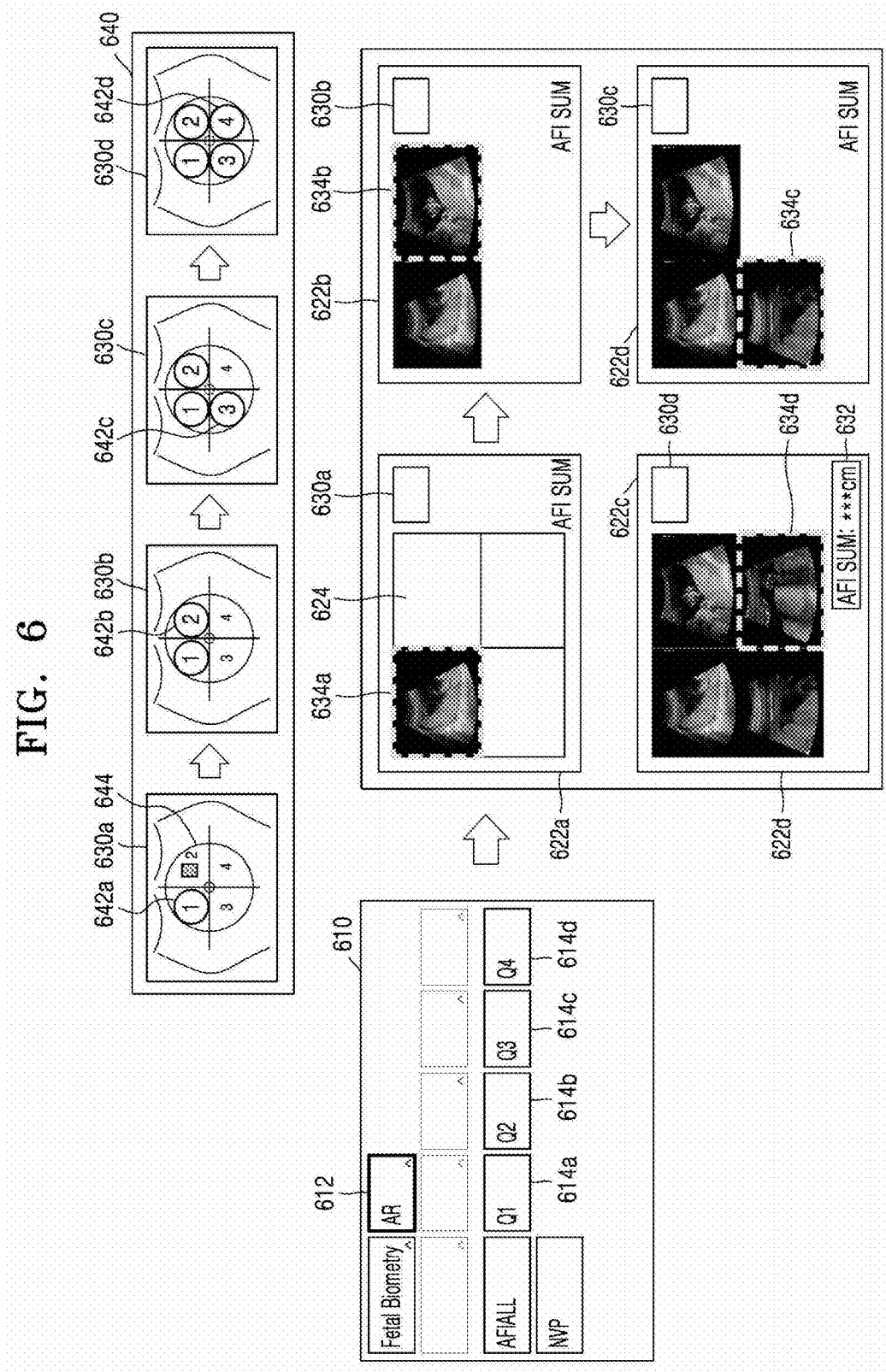
FIG. 6 illustrates a GUI view in a scan mode according to an embodiment of the disclosure.

FIG. 6 illustrates a GUI view in a scan mode according to an embodiment of the disclosure.

According to an embodiment, when a scanning protocol for calculating a resulting value is selected in a scan mode, the ultrasound imaging apparatus 300 may automatically display a plurality of relevant medical images used to calculate the resulting value in a multi-view, and when capturing of the relevant medical images is completed, automatically display the calculated resulting value. The ultrasound imaging apparatus 300 may automatically display a multi-view of the relevant medical images used for calculating the resulting value based on a trigger condition that capturing of the relevant medical images is completed. An embodiment in which an AFI SUM value is calculated is mainly described with reference to FIG. 6.

The ultrasound imaging apparatus 300 provides a measurement GUI 610. When a resulting value 612 is selected in the measurement GUI 610, the ultrasound imaging apparatus 300 executes a scanning protocol for obtaining the resulting value 612. When a process of obtaining an AFI SUM value is selected, the ultrasound imaging apparatus 300 executes a scanning protocol for calculating AFI values in a plurality of quadrants of a pregnant woman's abdomen. By sequentially selecting buttons 614a through 614d respectively corresponding to quadrants Q1 through Q4 in the measurement GUI 610, the user may obtain relevant medical images 634a through 634d for respectively measuring AFI values in the quadrants Q1 through Q4 and AFI values AFI_Q1 through AFI_Q4.

When each of the relevant medical images 634a through 634d respectively corresponding to the quadrants Q1 through Q4 and its corresponding AFI value AFI_Q1, AFI_Q2, AFI_Q3, or AFI_Q4 are obtained, the ultrasound imaging apparatus 300 automatically displays the obtained relevant medical image 634a, 634b, 634c, or 634d and the corresponding AFI value AFI_Q1, AFI_Q2, AFI_Q3, or AFI_Q4 in multi-views 622a through 622d. The ultrasound imaging apparatus 300 may set a plurality of regions, i.e., first through fourth regions 624 in advance in each of the multi-views 622a through 622d and then set a relevant medical image corresponding to each of the first through fourth regions 624. For example, the multi-views 622a through 622d may each have the first through fourth regions 624 that are respectively set as the relevant medical images 634a through 634d for measuring the AFI values AFI_Q1 through AFI_Q4, respectively. Each time a relevant medical image for calculating a resulting value is obtained, the ultrasound imaging apparatus 300 may display the obtained relevant medical image in a region corresponding to the relevant medical image. For example, when the medical image 634a for measuring the AFI value AFI_Q1 is obtained during scanning, the ultrasound imaging apparatus 300 places the medical image 634a in a region corresponding to the AFI value AFI_Q1.

As the scanning proceeds, relevant medical images are sequentially placed in corresponding regions of the multi-views 622a through 622d. The user may recognize how far the scanning has progressed by viewing relevant medical images placed in the multi-views 622a through 622d. Because the ultrasound imaging apparatus 300 automatically places relevant medical images in corresponding regions of the multi-views 622a through 622d based on attributes Q1, Q2, Q3, and Q4 of the relevant medical images, the multi-views 622a, 622b, 622c, and 622d may be easily provided even when the user performs a medical imaging scan in any order desired by the user.

Each time one of the relevant medical images 634a through 634d is obtained, a measurement value is obtained from the medical image. The measurement value may be obtained based on measurement points manually input by the user. The measurement value may be stored together with the medical image. According to an embodiment, the ultrasound imaging apparatus 300 may display, in the multi-views 622a through 622d, a measurement value obtained from each of the relevant medical images 634a through 634d together with the relevant medical image 634a, 634b, 634c, or 634d.

According to an embodiment, when obtaining of the relevant medical images 634a, 634b, 634c, and 634d and measurement values for calculating a resulting value is completed, the ultrasound imaging apparatus 300 displays a resulting value 632 in the multi-view 622a, 622b, 622c, or 622d. The ultrasound imaging apparatus 300 may automatically detect that the process of obtaining the relevant medical images 634a through 634d and the measurement values is completed, calculate the resulting value 632, and automatically display the resulting value 632 in the multi-view 622a, 622b, 622c, or 622d. The resulting value 632 may be displayed in a region of the multi-view 622a, 622b, 622c, or 622d or as a pop-up form or the like.

According to an embodiment, the ultrasound imaging apparatus 300 may respectively display pieces of scanning progress information 630a through 630d together in the multi-views 622a, 622b, 622c, and 622d. The pieces of scanning progress information 630a through 630d each include information about types of the relevant medical images 634a through 634d required for calculating a resulting value and information indicating how far the process of obtaining the required relevant medical images 634a through 634d has progressed. According to an embodiment, the pieces of scanning progress information 630a through 630d may each indicate information about a region of an object being scanned and be provided in a form of displaying an scan region where scanning is completed. For example, for measurement of AFI_SUM, the ultrasound imaging apparatus 300 display scan region information 644 regarding four quadrants into which the pregnant woman's abdomen is divided. As scanning proceeds, the ultrasound imaging apparatus 300 may display indicators 642a through 642d in the four quadrants where the scanning is completed. The ultrasound imaging apparatus 300 may update the pieces of scanning progress information 630a through 630d as the scanning proceeds and display the updated pieces of scanning progress information 630a through 630d together with the multi-views 622 through 622d.

According to an embodiment, the ultrasound imaging apparatus 300 may include a plurality of displays, and the multi-views 622a through 622d may be displayed on one of the displays of the ultrasound imaging apparatus 300. In this case, a GUI for displaying a real-time scan image may be provided on one of the displays other than the display on which the multi-views 622a through 622d are displayed.

According to another embodiment, a multi-view GUI representing the multi-views 622a through 622d may be alternately displayed with a scan GUI for displaying a real-time scan image. The multi-view GUI and the scan GUI may be switched between each other by an input of a control signal and then displayed.

Figure 7:
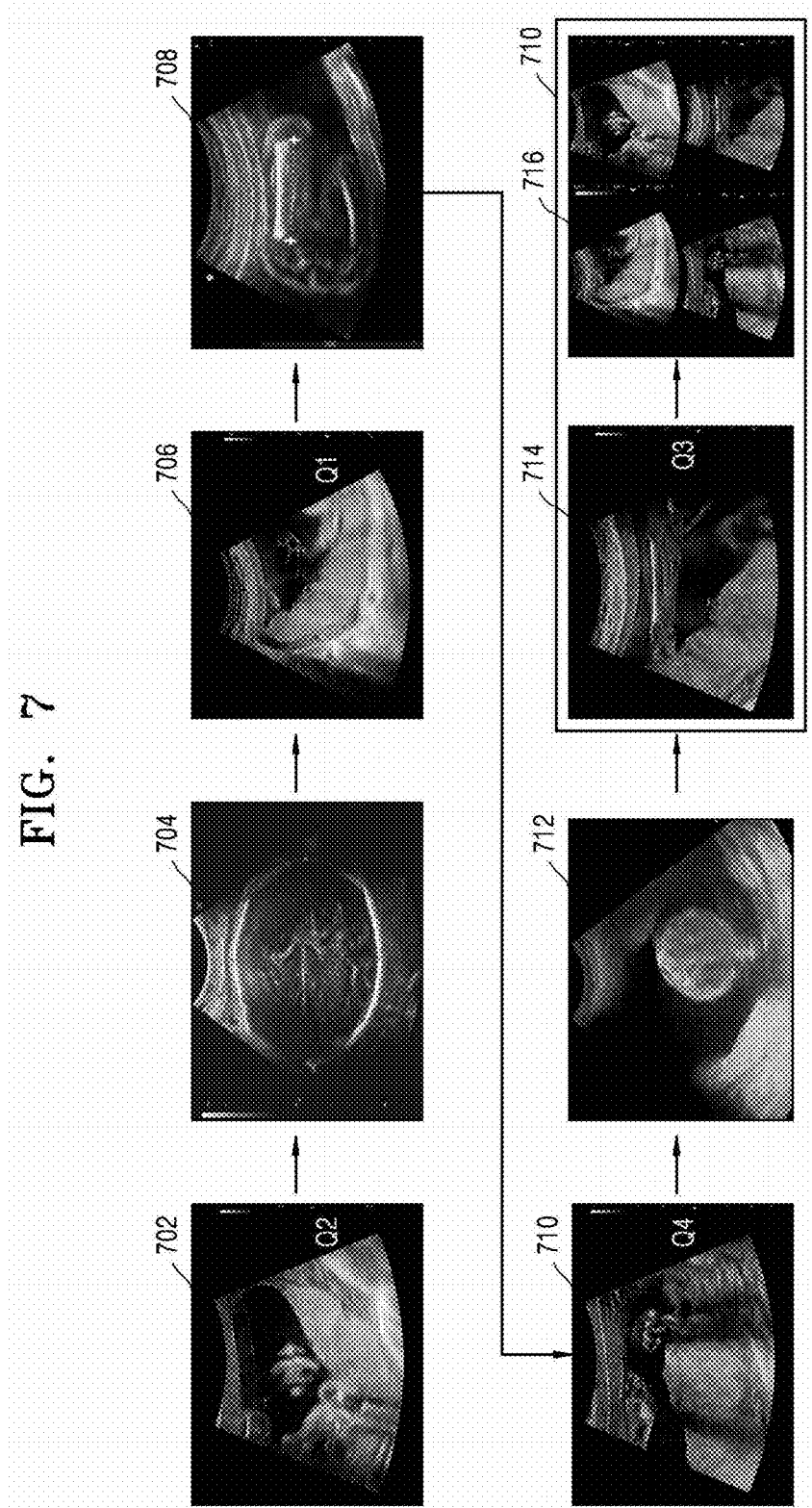
FIG. 7 illustrates a scanning process according to an embodiment of the disclosure.

FIG. 7 illustrates a scanning process according to an embodiment of the disclosure.

According to an embodiment, the ultrasound imaging apparatus 300 may provide a scanning GUI for medical images and automatically generate and display a multi-view 716 when detecting that a scan for the medical images is completed. An embodiment in which an AFI SUM value is calculated is mainly described with reference to FIG. 7.

The ultrasound imaging apparatus 300 obtains each medical image based on a freeze input. For example, when the user inputs a freeze during scanning of the object, a medical image 702 of a region Q2 is stored, and AFI_Q2 is measured in the medical image of the region Q2. The ultrasound imaging apparatus 300 may recognize that the medical image 702 is an image of the region Q2 automatically or according to a user input. When the measurement of AFI_Q2 is completed, the ultrasound imaging apparatus 300 displays a real-time scan image 704 again. When a freeze input is detected during capturing of the real-time scan image 704, an additional relevant medical image 706 is obtained. When the medical image 706 corresponds to a region Q1, a measurement value of AFI_Q1 is obtained based on the medical image 706. When the measurement of AFI_Q1 is completed, the ultrasound imaging apparatus 300 displays a real-time scan image 708 again. When a freeze input is detected during capturing of the real-time scan image 708, an additional relevant medical image 710 is obtained. When the medical image 710 corresponds to a region Q4, a measurement value of AFI_Q4 is obtained based on the medical image 710. When the measurement of AFI_Q4 is completed, the ultrasound imaging apparatus 300 displays a real-time scan image 712 again. When a freeze input is detected during capturing of the real-time scan image 712, an additional relevant medical image 714 is obtained. If the medical image 714 corresponds to a region Q3, a measurement value of AFI_Q3 is obtained based on the medical image 714. When the measurement of AFI_Q3 is completed, the ultrasound imaging apparatus 300 detects that obtaining of the relevant medical images and measurement values for calculating an AFI_SUM value is completed and then calculates the AFI_SUM value. After calculating the AFI_SUM value, the ultrasound imaging apparatus 300 generates the multi-view 716 and displays the calculated resulting value, a plurality of relevant medical images, and a plurality of measurement values. The ultrasound imaging apparatus 300 according to an embodiment of the disclosure is different from the existing ultrasound imaging apparatus in that the ultrasound imaging apparatus 300 automatically displays the multi-view 716 without displaying another real-time scan image after obtaining the measurement value from the last relevant medical image 714.

Figure 8:
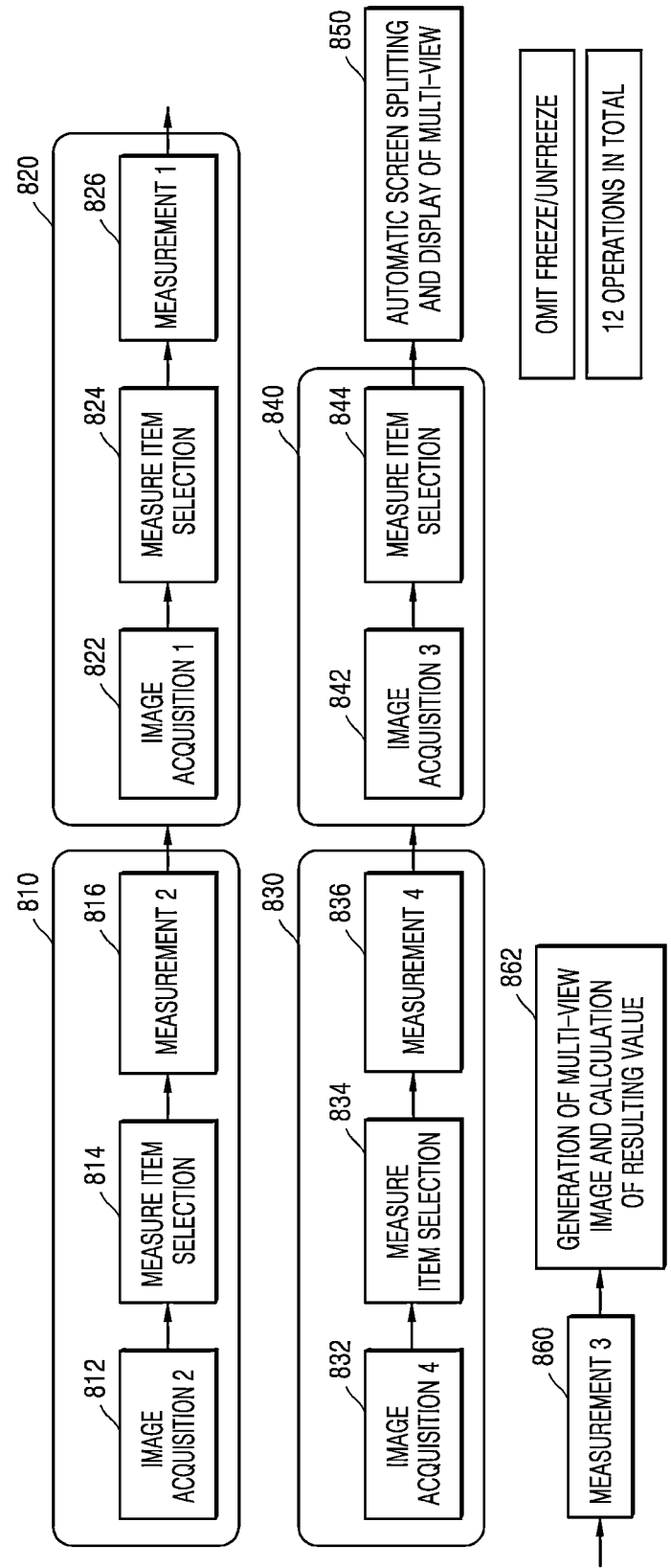
FIG. 8 illustrates a process of capturing an ultrasound medical image, according to an embodiment of the disclosure.

FIG. 8 illustrates a process of capturing an ultrasound medical image, according to an embodiment of the disclosure.

According to an embodiment of the disclosure, during a process of obtaining a plurality of medical images and a plurality of measurement values, a measurement value for a last medical image may be obtained in a multi-view display. An embodiment in which a resulting value is calculated based on four medical images and four measurement values is mainly described with reference to FIG. 8.

According to an embodiment, the ultrasound medical apparatus 300 sequentially performs a process of obtaining medical images and measurement values. For example, the ultrasound medical apparatus 300 may perform a process 810 of obtaining a second medical image, a process 820 of obtaining a first medical image, and a process 830 of a fourth medical image. In the process 810, the ultrasound medical apparatus 300 obtains the second medical image based on a freeze input (812) and obtains a second measurement value corresponding to the second medical image based on a user's selection 814 of Measure Item (816). Furthermore, in the process 820, the ultrasound medical apparatus 300 obtains the first medical image based on a freeze input (822) and obtains a first measurement value corresponding to the first medical image based on a user's selection 824 of Measure Item (826). Furthermore, in the process 830, the ultrasound medical apparatus 300 obtains the fourth medical image based on a freeze input (832) and obtains a fourth measurement value corresponding to the fourth medical image based on a user's selection 834 of Measure Item (836).

Next, in a process 840 of obtaining a third medical image, which is a last relevant medical image, the ultrasound imaging apparatus 300 obtains the third medical image based on a freeze input (842) and detects, based on a user's selection 844 of Measure Item, that capturing of all the relevant medical images required to calculate a resulting value is completed. When capturing of all relevant medical images is completed, the ultrasound imaging apparatus 300 automatically splits a screen and displays a multi-view (850). Thereafter, the ultrasound imaging apparatus 300 obtains a third measurement value from the third medical image in the multi-view (860) and completes generation of a multi-view image and a calculation process for a resulting value (862).

According to an embodiment of the disclosure, the ultrasound imaging apparatus 300 does not require the user to directly split the screen into a plurality of regions and retrieve and display a medical image for each of the regions on the screen, such that the user may easily utilize a multi-view display. In addition, according to an embodiment of the disclosure, it is possible to skip a process of the user directly splitting the screen into regions and placing a medical image in each of the regions, thereby significantly reducing the number of user manipulations.

Figure 9:
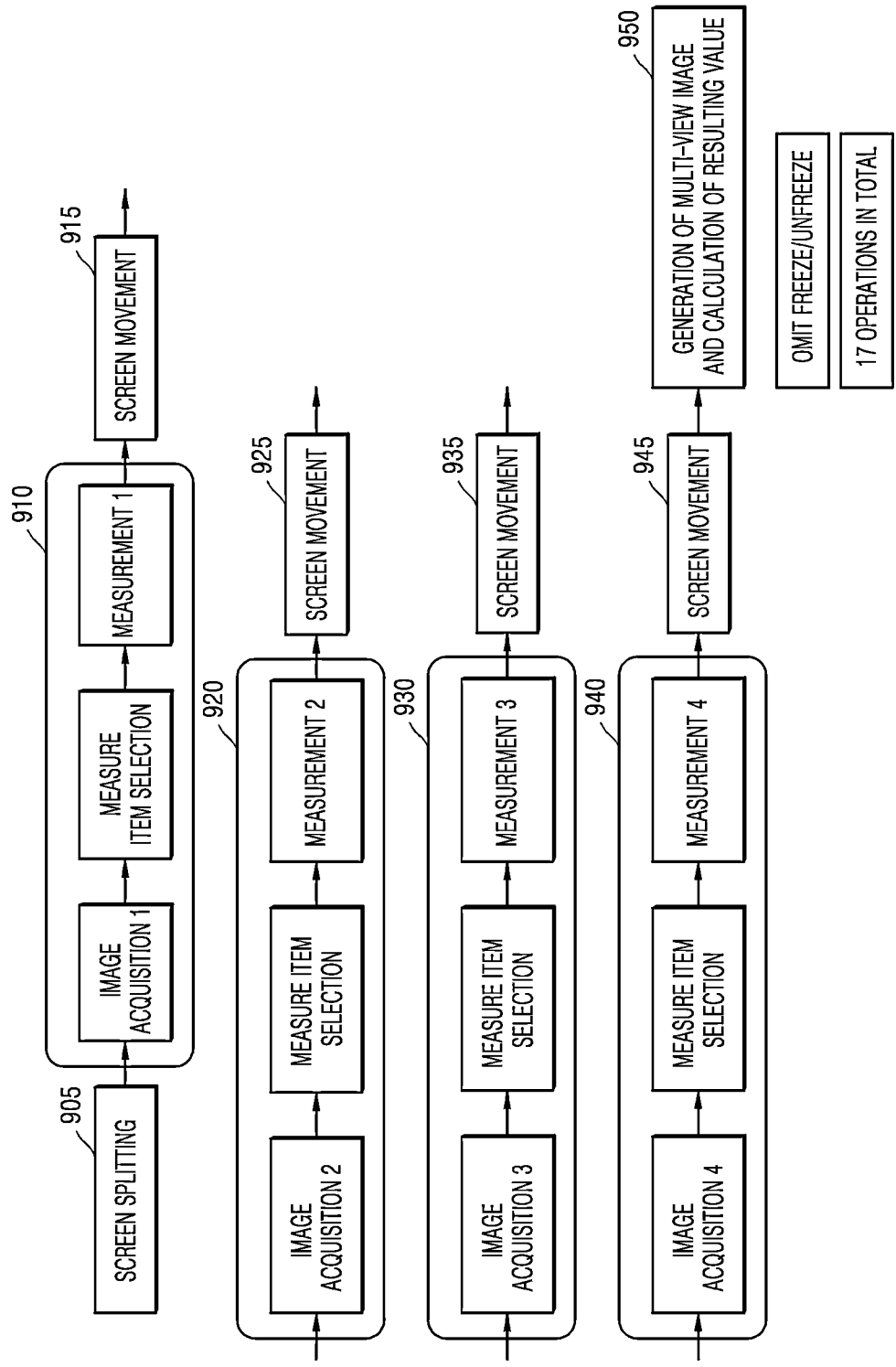
FIG. 9 illustrates manipulation operations performed by a user, according to a comparative example.

FIG. 9 illustrates manipulation operations performed by a user according to a comparative example. Effects achieved by embodiments of the disclosure will now be described by comparing the embodiment described with reference to FIG. 8 with the comparative example of FIG. 9.

In both the embodiment of the disclosure described with reference to FIG. 8 and the comparative example of FIG. 9, it is assumed that a resulting value is calculated based on a total of four relevant medical images and four measurement values. In FIGS. 8 and 9, freeze input and unfreeze operations are omitted.

According to the embodiment illustrated in FIG. 8, manipulations by the user include a total of twelve (12) operations 812, 814, 816, 822, 824, 826, 832, 834, 836, 842, 844, and 860, excluding operations automatically performed by the ultrasound imaging apparatus 300, i.e., the operation 850 of automatically splitting the screen and displaying a multi-view and the operation 862 of generating a multi-view image and performing a calculation process for a resulting value.

On the other hand, according to the comparative example of FIG. 9, the number of manipulations by the user increases because the user has to directly perform a screen splitting operation 905 and screen movement operations 915, 925, and 935 for setting a region corresponding to a next image to be captured in a multi-view. According to the comparative example of FIG. 9, the user first splits the screen into a number of regions corresponding to the number of medical images to be obtained (905). For example, when four medical images are required, the user may select screen splitting to divide the screen into four regions. Next, the user performs an operation 910 of obtaining a first medical image and a first measurement value. When the operation 910 of obtaining the first medical image and the first measurement value is completed, the user returns to a multi-view GUI and selects a region corresponding to a next medical image to be captured (915). The user may move an active region by clicking a setting or screen splitting button and captures a next medical image. Subsequently, the user performs an operation 920 of obtaining a second medical image and a second measurement value and then performs again a screen movement operation 925. Thereafter, the user performs an operation 930 of obtaining a third medical image and a third measurement value and then performs again a screen movement operation 935. Next, the user performs an operation 940 of obtaining a fourth medical image and a fourth measurement value and then performs again a screen movement operation 945. When obtaining of the four medical images and the four measurement values is completed and screen movement is performed, the ultrasound imaging apparatus 300 provides a GUI view in which a multi-view image and a calculated resulting value are displayed.

According to the comparative example of FIG. 9, the user has to directly manipulate the screen splitting operation 905, the four operations 910, 920, 930, and 940 of obtaining a medical image and a measurement value, and the four screen movement operations 915, 925, 935 and 945. Each of the four operations 910, 920, 930, and 940 of obtaining a medical image and a measurement value include three user manipulations. Thus, user manipulations according to the comparative example of FIG. 9 include a total of 17 operations.

As described above, for the same operation of calculating a resulting value, 12 user manipulations are required according to an embodiment of the disclosure while 17 user manipulations are required according to the comparative example. Thus, according to an embodiment of the disclosure, the number of user manipulations may be significantly reduced.

Figure 10:
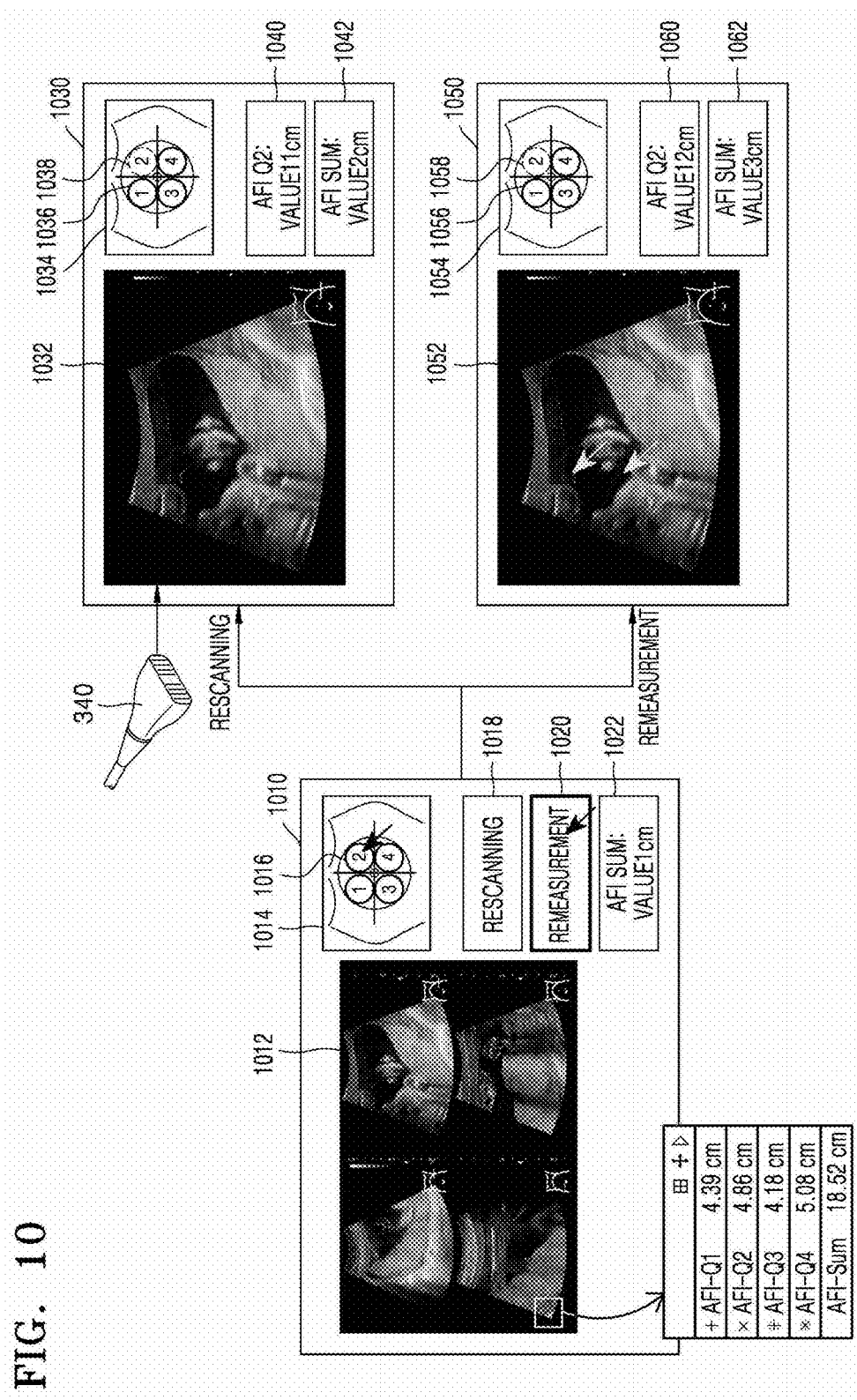
FIG. 10 illustrates a process of performing rescanning or remeasurement in a scan mode, according to an embodiment of the disclosure.

FIG. 10 illustrates a process of performing rescanning or remeasurement in a scan mode, according to an embodiment of the disclosure.

According to an embodiment of the disclosure, the ultrasound imaging apparatus 300 may provide a function of recapturing a relevant medical image or a function of remeasuring a required value. The ultrasound imaging apparatus 300 may display a multi-view image 1012, at least one measurement value, and a resulting value 1022 in a third GUI view 1010 and provide at least one of a rescanning menu 1018 and a remeasurement menu 1020, or a combination thereof. The third GUI view 1010 may provide a scan region selection menu 1014 for selecting a medical image to be recaptured from among a plurality of medical images or selecting a measurement value to be obtained again from among a plurality of measurement values. The scan region selection menu 1014 may include scan region indicators 1016 respectively corresponding to at least one captured relevant medical image. The ultrasound imaging apparatus 300 may receive a scan region selection input for selecting one of the scan region indicators 1016, and when the rescanning menu 1018 or remeasurement menu 1020 is selected, recapture a medical image corresponding to a region to be scanned, which is selected according to the selection input, or obtain again a measurement value corresponding to the selected region to be scanned. The scan region selection input and an input for selecting the rescanning menu 1018 or remeasurement menu 1020 may be received in an order different than described above. In other words, the user may first select the rescanning menu 1018 or the remeasurement menu 1020 and then perform the scan region selection input.

According to an embodiment, when the rescanning menu 1018 is selected, the ultrasound imaging apparatus 300 performs another ultrasound scan. The ultrasound imaging apparatus 300 displays a real-time scan image 1032 in a rescanning GUI 1030. Furthermore, the ultrasound imaging apparatus 300 also provides information 1034 about a region to be rescanned in the rescanning GUI 1030. The ultrasound imaging apparatus 300 may display a scan region indicator 1038 corresponding to a region to be scanned, which is selected according to a scan region selection input, by using different attributes than those of another scan region indicator 1036. For example, when a region Q2 is selected as a region to be scanned, the ultrasound imaging apparatus 300 may display the scan region indicator 1038 for the region Q2 as a dashed line in the rescanning GUI 1030 while displaying the other scan region indicator 1036 for the remaining regions Q1, Q3, and Q4 as a solid line. As another example, the scan region indicator 1038 for the selected region to be scanned may be displayed differently than the other scan region indicator 1036 by using attributes such as color, size, font, shape, blinking, line thickness, etc.

According to an embodiment, the ultrasound imaging apparatus 300 may display, in the rescanning GUI 1030, information 1040 about a measurement value obtained from a relevant medical image being recaptured and information 1042 about a resulting value. The information 1040 about a measurement value obtained from a relevant medical image being recaptured and the information 1042 about a resulting value may be updated accordingly as rescanning and remeasurement proceed.

According to an embodiment, when the remeasurement menu 1020 is selected, the ultrasound imaging apparatus 300 additionally performs a process of obtaining a measurement value from a relevant medical image. The ultrasound imaging apparatus 300 may display, in a remeasurement GUI 1050, a relevant medical image 1052 corresponding to a region to be scanned, selected by the user. The ultrasound imaging apparatus 300 retrieves and displays the relevant medical image 1052 stored in the storage 330. Furthermore, the ultrasound imaging apparatus 300 provides remeasurement region information 1054 in the remeasurement GUI 1050. The ultrasound imaging apparatus 300 may display a measurement region indicator 1058 corresponding to a region that is to undergo measurement, which is selected according to a measurement region selection input, by using different attributes than those of another measurement region indicator 1056.

According to an embodiment, the ultrasound imaging apparatus 300 may display, in the remeasurement GUI 1050, information 1060 about a measurement value obtained from a relevant medical image undergoing remeasurement and information 1062 about a resulting value. The information 1060 about a measurement value in a relevant medical image undergoing remeasurement and the information 1062 about a resulting value may be updated accordingly as the remeasurement proceeds.

Figure 11:
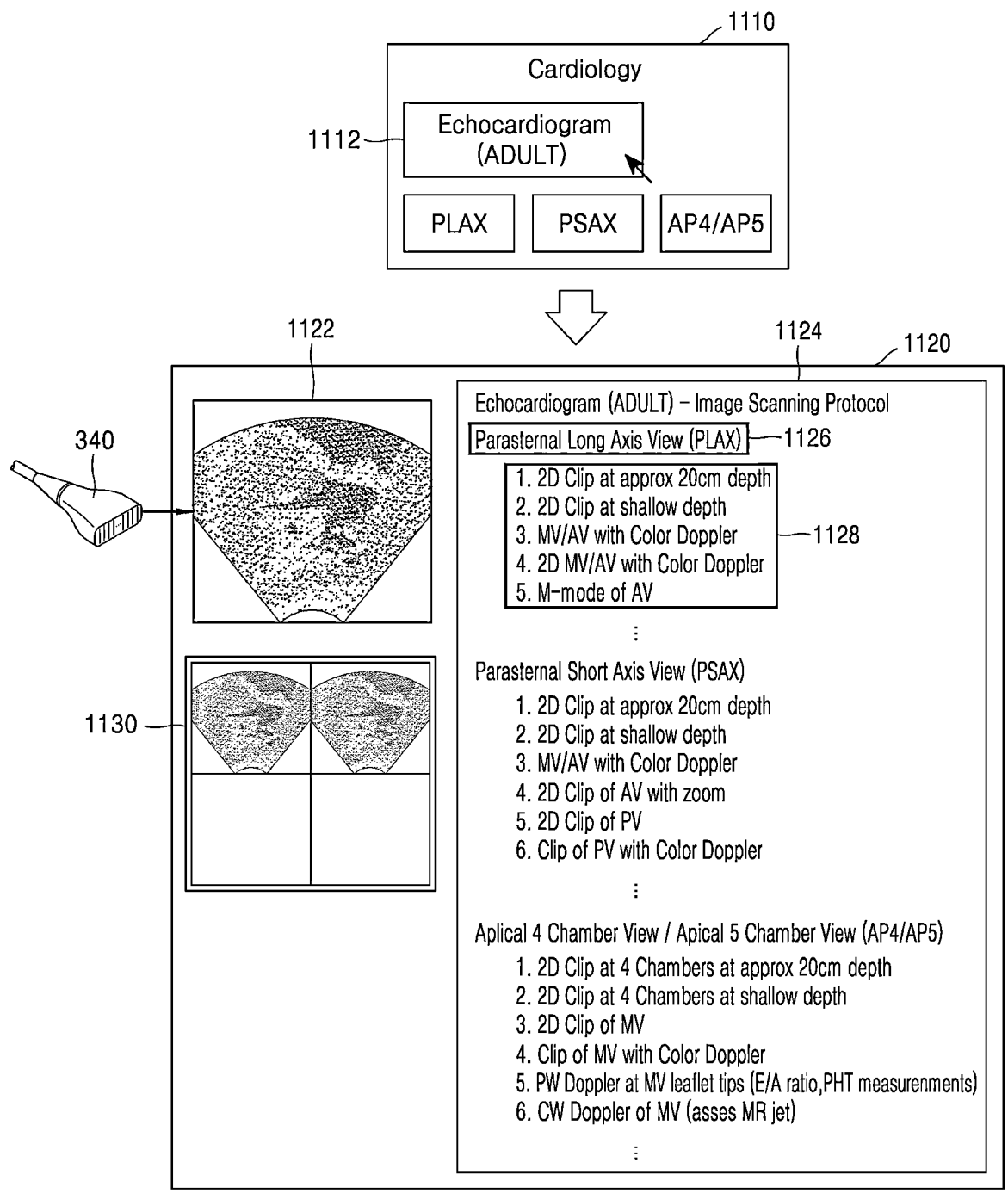
FIG. 11 illustrates a process of performing a scanning protocol for obtaining a resulting value from multiple measurement values, according to an embodiment of the disclosure.

FIG. 11 illustrates a process of performing a scanning protocol for obtaining a resulting value from multiple measurement values, according to an embodiment of the disclosure.

When multiple image-capturing operations and multiple measurements are required to obtain a single resulting value, the user has difficulties in performing all the image-capturing operations and measurements thoroughly. According to embodiments of the disclosure, when the user selects a scanning protocol for calculating a resulting value, information (e.g., 1124) about a list of image-capturing operations and measurements required in the scanning protocol.

An embodiment in which echocardiography is performed is mainly described with reference to FIG. 11.

Multiple image-capturing operations and measurements are required to perform echocardiography, and there are many lists of the required image-capturing operations and required measurements. For example, the echocardiography requires medical images obtained in three (3) views and forty-two (42) measurements. In the echocardiography, a size or volume of the left atrium is an important indicator of a pressure, a diastolic function, and a prognostic value of the left ventricle. The volume of the left atrium is calculated by measuring a cross-section of the left atrium in the parasternal long axis view (PLAX) and length and width of the left atrium in the apical 4 chamber (A4C) view.

According to an embodiment of the disclosure, when the user selects one scanning protocol 1112 from a protocol selection GUI 1110, the ultrasound imaging apparatus 300 displays, in a scan mode GUI 1120, a list 1124 of required ultrasound images and required measurement values together with a real-time scan image 1122. The list 1124 of required ultrasound images and required measurement values include information 1126 about required scanning views and information 1128 about required measurement values.

According to an embodiment, the ultrasound imaging apparatus 300 provides a multi-view 1130 for displaying relevant medical images obtained in the scan mode GUI 1120. Properties of a relevant image corresponding to each region of the multi-view 1130 may be predefined. For example, in the case of echocardiography, regions of the multi-view 1130 may respectively correspond to the PLAX, parasternal short axis view (PSAX), and apical 4 chamber view (AP4)/apical 5 chamber view (AP5). As a scan proceeds, the ultrasound imaging apparatus 300 may place an obtained ultrasound image in each region of the multi-view 1130.

For example, as the scan and measurement proceed, the ultrasound imaging apparatus 300 may provide information indicating that a scan or measurement has been completed for a required ultrasound image or measurement value that has been captured or obtained from among the list 1124 of required ultrasound images and required measurement values. For example, to provide such information, the ultrasound imaging apparatus 300 may place a preset indicator on a required ultrasound image or measurement value that has been captured or obtained, change a color of a text of an item corresponding to the required ultrasound image or measurement value differently than items corresponding to the other ultrasound images or measurement values in the list 1124, or place a strikethrough line over the item corresponding to the required ultrasound image or measurement value.

When a last measurement is completed in the A4C view, the ultrasound imaging apparatus 300 displays, on a single screen, a cross-sectional image of the left atrium and a measurement value obtained in LAX (long-axis view) as well as the volume of the left atrium. As another example, the ultrasound imaging apparatus 300 may simultaneously display relevant images before measuring the length and width of the left atrium in the A4C view.

Figure 12:
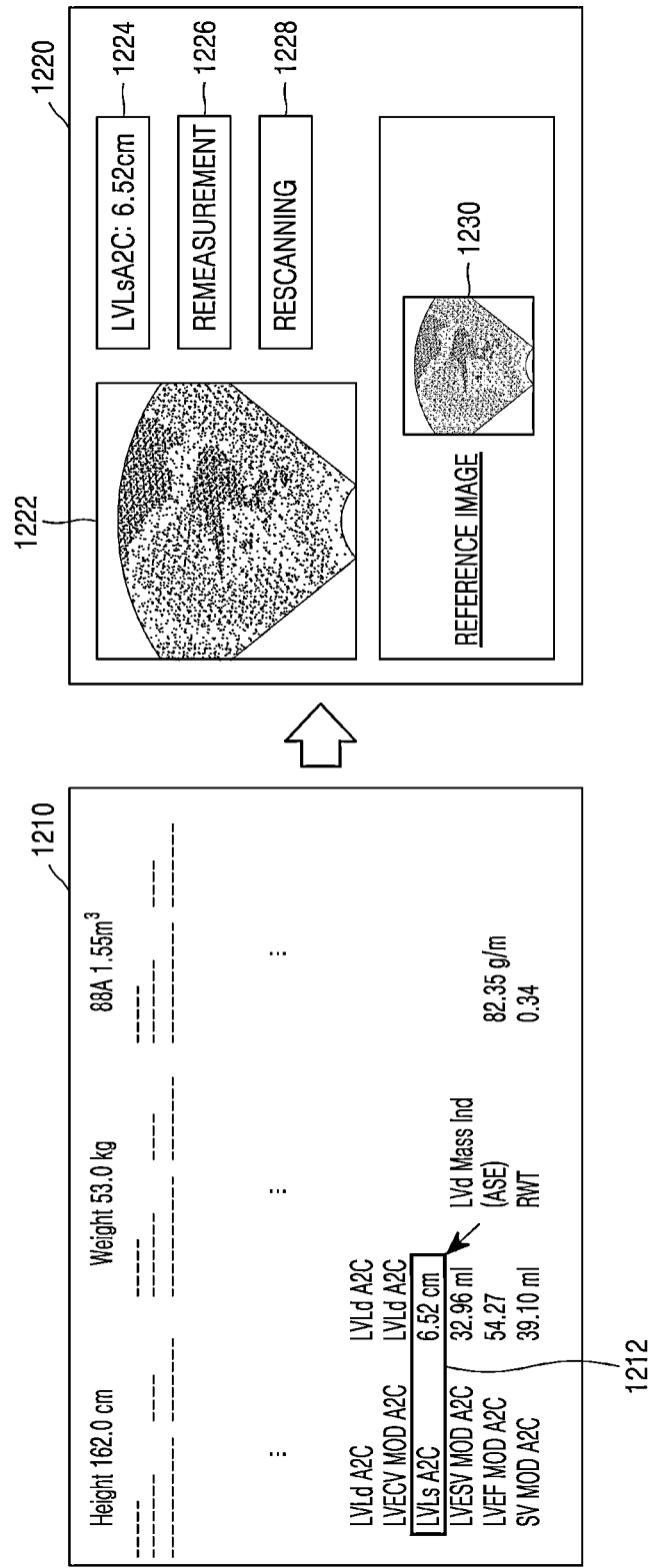
FIG. 12 illustrates a process of selecting a resulting value and displaying a plurality of relevant medical images and a plurality of measurement values, according to an embodiment of the disclosure.

FIG. 12 illustrates a process of selecting a resulting value and displaying a plurality of relevant medical images and a plurality of measurement values, according to an embodiment of the disclosure.

According to an embodiment of the disclosure, the ultrasound imaging apparatus 300 provides a report GUI 1210 that provides a list of measurement values used to calculate a resulting value. The report GUI 1210 provides a list of measurement values used to calculate a resulting value and their corresponding numerical values. For a composite measurement using multiple measurement values, several tens of measurement value lists are displayed in the report GUI 1210. According to an embodiment of the disclosure, when one measurement value 1212 is selected in the report GUI 1210, the ultrasound imaging apparatus 300 provides a relevant medical image retrieval GUI 1220 for displaying relevant medical images used to obtain the measurement value 1212. In the report GUI 1210, each measurement value may be linked to a medical image from which the measurement value is obtained.

The relevant medical image retrieval GUI 1220 displays a relevant medical image 1222 from which the measurement value 1212 selected by the user is obtained. Furthermore, the relevant medical image retrieval GUI 1220 displays information 1224 about the measurement value 1212 selected by the user. The relevant medical image retrieval GUI 1220 may also provide a remeasurement function 1226 for obtaining a measurement value again from the relevant medical image 1222 and a rescanning function 1228. Because the remeasurement function 1226 or rescanning function 1228 is substantially similar to that described with reference to FIG. 10, a detailed description will be omitted here.

According to an embodiment, the ultrasound imaging apparatus 100 provides information 1230 about a reference image related to the selected measurement value 1212. The information 1230 about the reference image 1230 may be provided in the form of a thumbnail, a description of the reference image, a medical name for the reference image, etc. The ultrasound imaging apparatus 300 may store information about a view or properties of a relevant medical image corresponding to each measurement value (e.g., 1212), and define and provide a relevant reference image based on the stored information.

Figure 13:
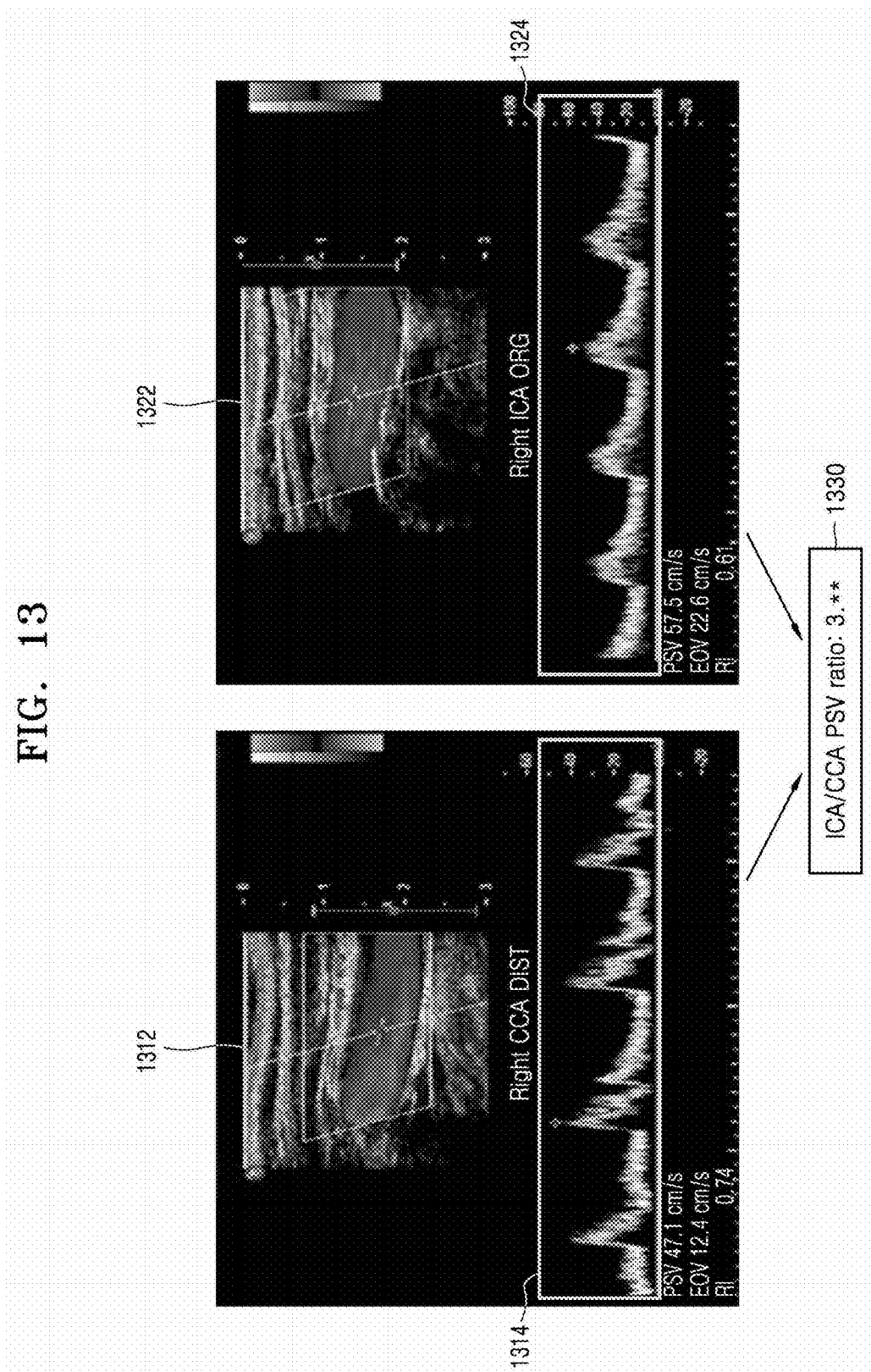
FIG. 13 illustrates a process of measuring a stenosis rate for an internal carotid artery (ICA), according to an embodiment of the disclosure.

FIG. 13 illustrates a process of measuring a rate of internal carotid artery (ICA) stenosis, according to an embodiment of the disclosure.

The rate of ICA stenosis may be diagnosed based on ICA to common carotid artery (ICA/CCA) peak systolic velocity (PSV) ratio. The user may measure the ICA/CCA PSV ratio by sequentially measuring a PSV of CCA and a PSV of ICA in a pulsed wave (PW) mode.

The ultrasound imaging apparatus 300 measures a PSV of CCA in a Doppler image 1312 of CA and a PSV of ICA in a Doppler image 1322 of the ICA. To measure the ICA/CCA PSV ratio, it is often necessary to refer to a Doppler spectrum 1314 of the CCA and a Doppler spectrum 1324 of the ICA, both spectra representing blood flow velocities over time. When measurements of CCA PSV and ICA PSV are completed, the ultrasound imaging apparatus 300 calculates an ICA/CCA PSV ratio and displays ICA/CCA PSV ratio information 1330.

Figure 14:
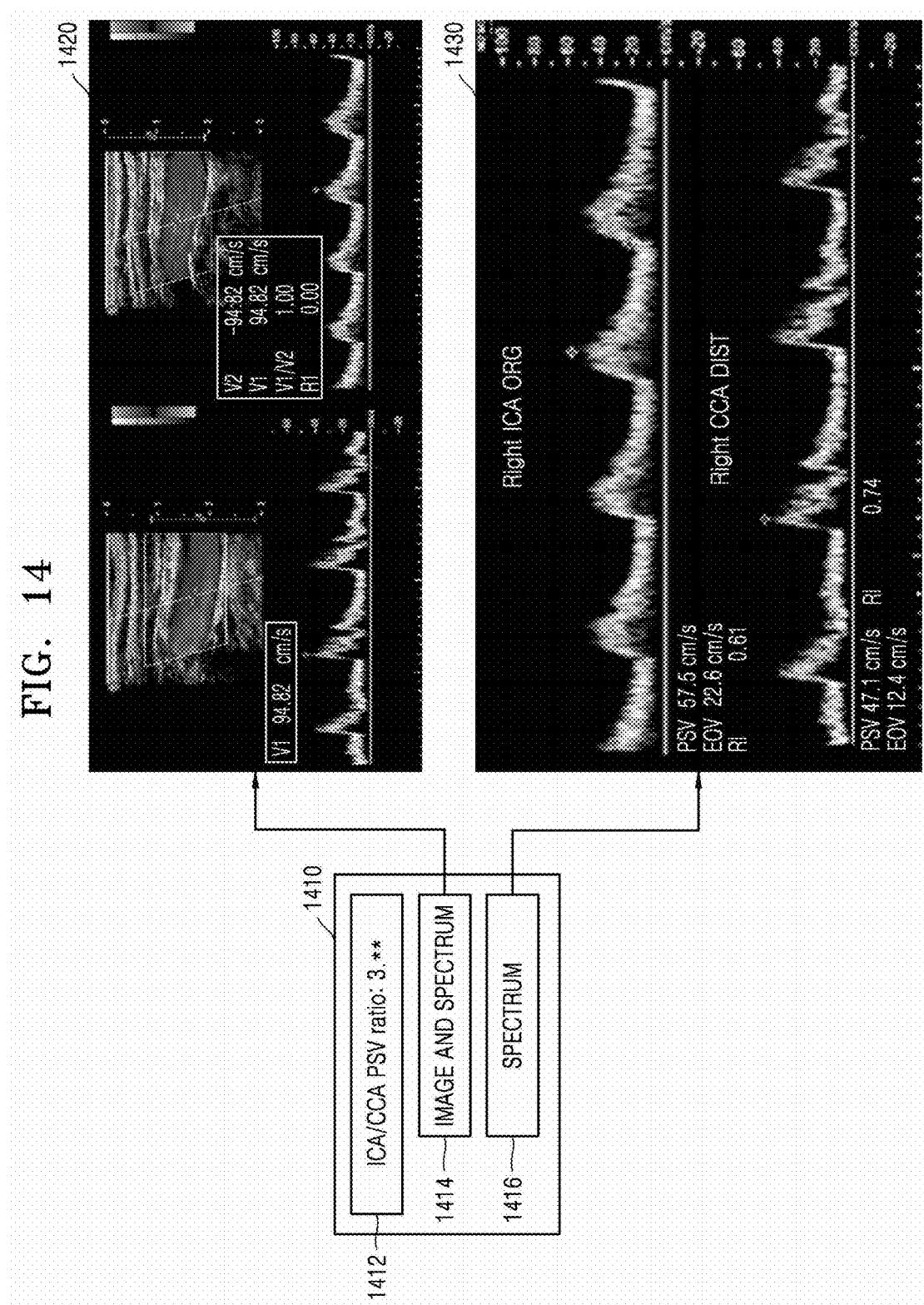
FIG. 14 illustrates a process of displaying a medical image and a measurement value related to an ICA/common carotid artery (CCA) peak systolic velocity (PSV) ratio, according to an embodiment of the disclosure.

FIG. 14 illustrates a process of displaying a medical image and a measurement value related to an ICA/CCA PSV ratio, according to an embodiment of the disclosure.

According to an embodiment of the disclosure, the ultrasound imaging apparatus 300 provides a menu for displaying a relevant image or blood flow spectrum while providing information 1412 about the ICA/CCA PSV ratio in the GUI view 1410 in a GUI view 1410.

According to an embodiment, the GUI view 1410 provides an image and spectrum menu 1414 for simultaneously displaying an image and a spectrum. When the image and spectrum menu 1414 is selected by the user, the ultrasound imaging apparatus 300 provides a complex multi-view 1420 in which a Doppler image of CCA, a spectrum of the CCA, a Doppler image of ICA, and a spectrum of the ICA are displayed together.

According to an embodiment, the GUI view 1410 provides a spectrum menu 1416 for simultaneously displaying the spectrum of the CCA and the spectrum of the ICA. When the spectrum menu 1416 is selected by the user, the ultrasound imaging apparatus 300 provides a spectrum multi-view 1430 in which the spectrum of the CCA and the spectrum of the ICA are displayed together. In the spectrum multi-view 1430, a PSV value of the CCA and a PSV value of the ICA may be displayed together with corresponding blood flow spectra.

Figure 15:
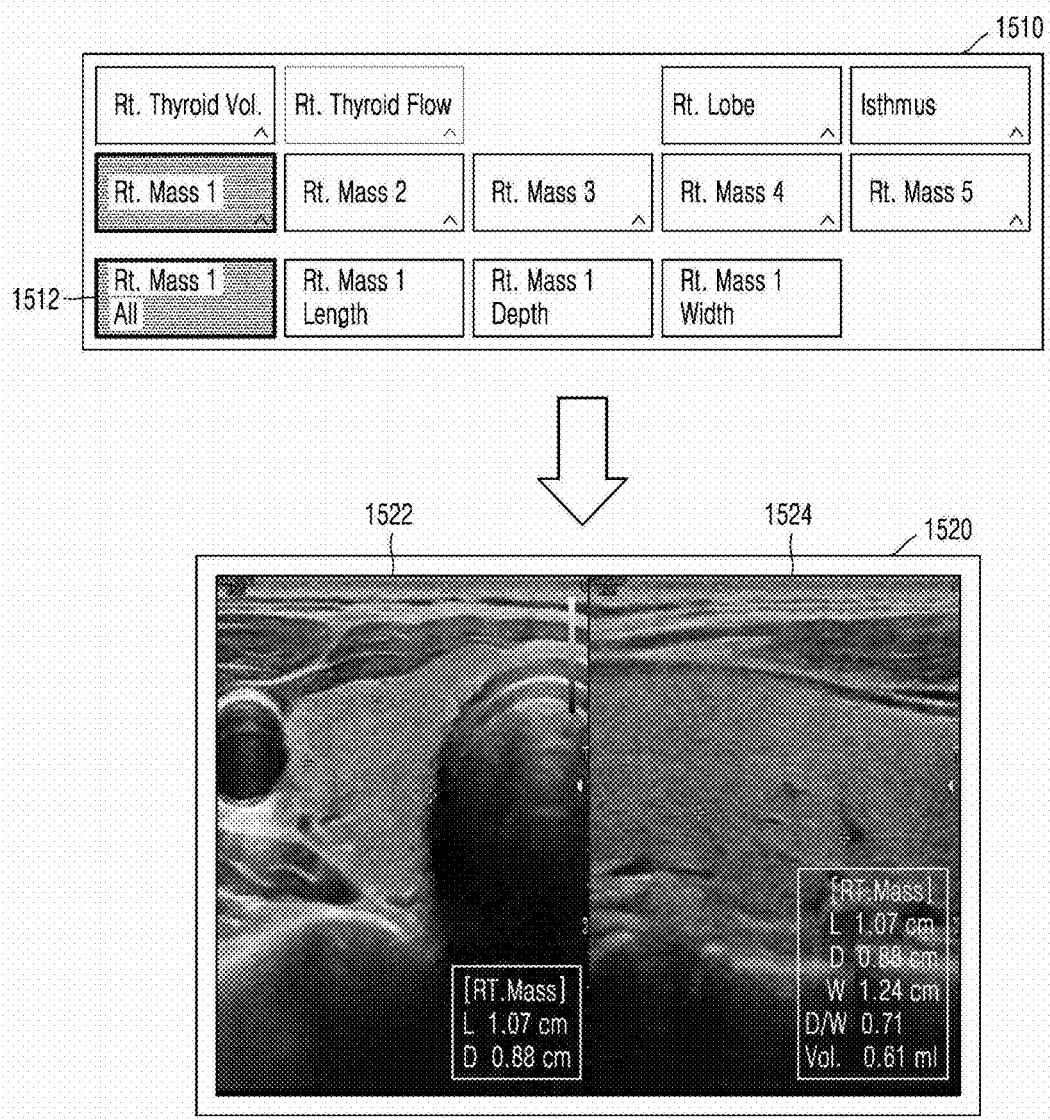
FIG. 15 illustrates a process of displaying a plurality of relevant medical images, according to an embodiment of the disclosure.

FIG. 15 illustrates a process of displaying a plurality of relevant medical images, according to an embodiment of the disclosure.

According to an embodiment of the disclosure, when a user selects a desired resulting value 1512 in a resulting value view GUI 1510, the ultrasound imaging apparatus 300 outputs a plurality of medical images 1522 and 1524 used to calculate the selected resulting value 1512 in the form of a multi-view GUI 1520. The multi-view GUI 1520 may have a form of a dual multi-view as shown in FIG. 15 or a quad multi-view.

Figure 16:
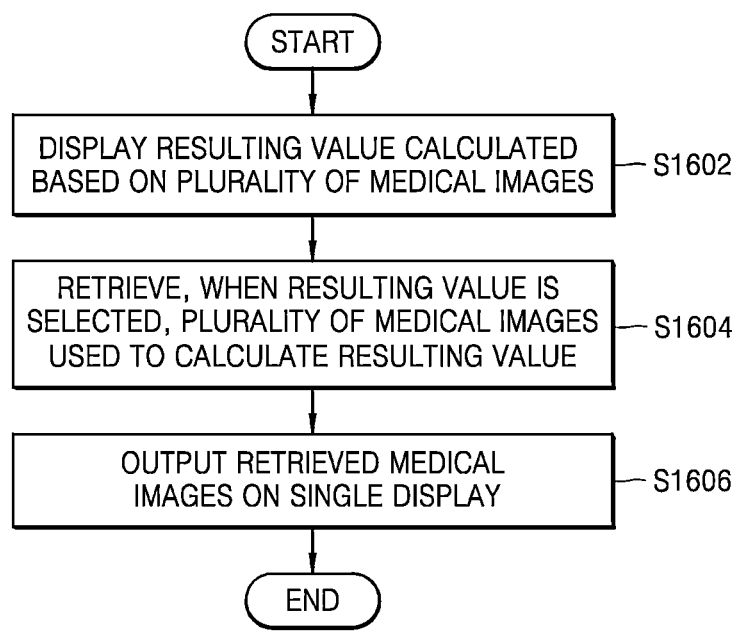
FIG. 16 is a flowchart of a control method of an ultrasound imaging apparatus, according to an embodiment of the disclosure.

FIG. 16 is a flowchart of a control method of an ultrasound imaging apparatus, according to an embodiment of the disclosure.

Operations of a control method of an ultrasound imaging apparatus according to the disclosure may be performed by various types of electronic devices including a processor. This specification mainly describes an embodiment in which the ultrasound imaging apparatus 300 performs a control method of an ultrasound imaging apparatus according to embodiments of the disclosure. Thus, embodiments described with respect to the ultrasound imaging apparatus 300 may be applied to embodiments described with respect to a control method of an ultrasound imaging apparatus. Conversely, embodiments described with respect to a control method of an ultrasound imaging apparatus may be applied to embodiments described with respect to the ultrasound imaging apparatus 300. Although it has been described that control methods of an ultrasound imaging apparatus according to embodiments of the disclosure are performed by the ultrasound imaging apparatus 300, embodiments are not limited thereto, and the methods may be performed by various types of electronic devices.

The ultrasound imaging apparatus displays, via an I/O interface, at least one resulting value calculated based on a plurality of medical images (S1602).

When a selection input for selecting one of the displayed at least one resulting value is received, the ultrasound imaging apparatus retrieves a plurality of measurement values and a plurality of relevant medical images required to calculate the selected resulting value (S1604). When the resulting value is selected, the ultrasound imaging apparatus determines and retrieves at least one measurement value required to calculate the resulting value. A measurement value required to calculate the resulting value may be determined from a list of values required for an equation for calculating the resulting value. Furthermore, the ultrasound imaging apparatus retrieves a measurement value for a patient corresponding to the resulting value, based on patient identification information corresponding to the resulting value. In addition, the ultrasound imaging apparatus retrieves a relevant medical image used to obtain a measurement value for the patient corresponding to the resulting value. The relevant medical image may be retrieved based on the patient identification information and a type of the measurement value. A file in which each resulting value is stored may also include a storage path information or identification information regarding at least one measurement value and at least one relevant medical image used to calculate the resulting value. In addition, each resulting value and at least one measurement value and at least one medical image corresponding to the resulting value may be stored and defined together with their acquisition dates and patient identification information.

The ultrasound imaging apparatus outputs the retrieved measurement values and medical images on a single display via an I/O interface (S1606). The retrieved medical images are respectively displayed in different regions of a GUI view. For example, the ultrasound imaging apparatus may define first through fourth regions that do not overlap one another in the GUI view and respectively display first through fourth medical images in the first through fourth regions.

Furthermore, the embodiments of the disclosure described with reference to FIGS. 3 through 15 may be applied to a control method of an ultrasound imaging apparatus. In addition, operations of the ultrasound imaging apparatus 300 described with reference to FIGS. 3 through 15 may be added as operations of a control method of an ultrasound imaging apparatus.

Moreover, embodiments of the disclosure may be implemented through non-transitory computer-readable recording media having stored thereon computer-executable instructions and data. The instructions may be stored in the form of program code, and when executed by a processor, generate a predefined program module to perform a preset operation. Furthermore, when executed by the processor, the instructions may perform preset operations according to embodiments.

According to embodiments of the disclosure, it is possible to provide an ultrasound imaging apparatus, a control method thereof, and a computer program for conveniently providing a plurality of relevant ultrasound images and a plurality of measurement values for a resulting value calculated by the ultrasound imaging apparatus based on the relevant ultrasound images and measurement values.

Furthermore, according to embodiments of the disclosure, it is possible to provide an ultrasound imaging apparatus, a control method thereof, and a computer program, which are capable of conveniently viewing, when a plurality of ultrasound images are captured and a plurality of measurement values are obtained to calculate a resulting value, the ultrasound images and the measurement values after completing a scan.

While embodiments of the disclosure have been particularly shown and described with reference to the accompanying drawings, it will be understood by those of ordinary skill in the art that various changes in form and details may be made therein without departing from essential characteristics or the spirit and scope of the disclosure as defined by the appended claims. The disclosed embodiments and all aspects thereof are examples only and are not to be construed as limiting the scope of the disclosure.

What is claimed is:

1. An ultrasound imaging apparatus comprising:
   an input/output interface;
   at least one storage configured to store instructions; and
   at least one processor configured to execute the instructions to:
   display, via the input/output interface, at least one resulting value calculated based on a plurality of medical images;
   when one of the at least one resulting value is selected by an input via the input/output interface, retrieve, from the at least one storage, a plurality of measurement values and the plurality of medical images used to calculate the selected resulting value; and
   output, via the input/output interface, the plurality of measurement values and the plurality of medical images on a single display,
   wherein the plurality of medical images are stored in the at least one storage together with at least one of attribute information, measurement value information, and scanning protocol information related to the plurality of medical images, or a combination thereof, and
   wherein the at least one processor is further configured to retrieve the plurality of medical images used to calculate the selected resulting value from the at least one storage, based on the at least one of the attribute information, the measurement value information, and the scanning protocol information related to the plurality of medical images, or the combination thereof, which are stored together with the plurality of medical images, wherein the at least one resulting value includes an internal carotid artery(ICA)/common carotid artery (CCA) peak systolic velocity (PSV) ratio between an ICA PSV and a CCA PSV, and wherein the at least one processor is further configured to execute the instructions to:

output the ICA/CCA PSV ratio via the input/output interface; and output, based on an input signal for selecting the ICA/CCA PSV ratio, a first ultrasound image in which the ICA PSV is measured, a time-blood flow velocity spectrum of ICA, a second ultrasound image in which the CCA PSV is measured, and a time-blood flow velocity spectrum of CCA on the single display.

2. The ultrasound imaging apparatus of claim 1, further comprising a probe configured to output ultrasound signals to an object and detect echo signals reflected from the object, wherein the at least one processor is further configured to execute the instructions to generate at least one ultrasound image based on the echo signals and store the at least one ultrasound image and at least one measurement value related to the at least one ultrasound image in the at least one storage.

3. The ultrasound imaging apparatus of claim 2, wherein the plurality of medical images include the at least one ultrasound image, and wherein the at least one processor is further configured to execute the instructions to:

calculate the at least one resulting value based on the at least one ultrasound image and the at least one measurement value related to the at least one ultrasound image; and display a real-time scan image and the at least one resulting value via the input/output interface.

4. The ultrasound imaging apparatus of claim 3, wherein the at least one processor is further configured to execute the instructions to:

display, based on a user input for selecting one of the displayed at least one resulting value, at least one ultrasound image related to the selected resulting value and at least one measurement value related to the selected resulting value; and provide, via the input/output interface, at least one of a rescanning menu for the at least one ultrasound image related to the selected resulting value and a remeasurement menu for the at least one measurement value related to the selected resulting value, or a combination of the rescanning menu and the remeasurement menu.

5. The ultrasound imaging apparatus of claim 4, wherein the at least one processor is further configured to execute the instructions to:

store an ultrasound image recaptured based on the rescanning menu in the at least one storage; and update the at least one measurement value related to the selected resulting value and the at least one resulting value based on the recaptured ultrasound image.

6. The ultrasound imaging apparatus of claim 1, wherein the at least one processor is further configured to execute the instructions to output, via the input/output interface, a required ultrasound image list and a required measurement value list corresponding to a scanning protocol selected via the input/output interface.

7. The ultrasound imaging apparatus of claim 6, wherein the at least one processor is further configured to execute the instructions to:

output, based on a selection of an ultrasound image item from the required ultrasound image list, an ultrasound image corresponding to the selected ultrasound image item via the input/output interface; and output, based on a selection of a measurement value item from the required measurement value list, an ultrasound image corresponding to the selected measurement value item via the input/output interface.

8. The ultrasound imaging apparatus of claim 2, wherein the at least one processor is further configured to execute the instructions to:

produce a first resulting value by using a first plurality of medical images generated based on the echo signals; and output, via the input/output interface, the first plurality of medical images required to produce the first resulting value and the first resulting value on a singlethe single display based on a trigger condition that the generating of the first plurality of medical images and the producing of the first resulting value are completed.

9. The ultrasound imaging apparatus of claim 1, wherein the at least one resulting value includes an internal carotid artery (ICA)/common carotid artery (CCA) peak systolic velocity (PSV) ratio between an ICA PSV and a CCA PSV, and wherein the at least one processor is further configured to execute the instructions to:

output the ICA/CCA PSV ratio via the input/output interface; and output, based on an input signal for selecting the ICA/CCA PSV ratio, a time-blood flow velocity spectrum of ICA and a time-blood flow velocity spectrum of CCA on the single display.

* * * * *

UNITED STATES PATENT AND TRADEMARK OFFICE
CERTIFICATE OF CORRECTION

| | | |
|---|---|---|
| PATENT NO. | : 12,042,332 B2 | Page 1 of 1 |
| APPLICATION NO. | : 17/132653 | |
| DATED | : July 23, 2024 | |
| INVENTOR(S) | : Sungah Park and Eunho Yang | |

It is certified that error appears in the above-identified patent and that said Letters Patent is hereby corrected as shown below:

In the Claims

Column 24, Line 34, Claim 8; Please delete "a singlethe single" and replace with --the single--

Signed and Sealed this
Twenty-fourth Day of December, 2024

Derrick Brent
*Acting Director of the United States Patent and Trademark Office*